United States Patent
Nishikori et al.

(10) Patent No.: US 11,320,735 B2
(45) Date of Patent: May 3, 2022

(54) RADIATION-SENSITIVE RESIN COMPOSITION, RESIST PATTERN-FORMING METHOD, ACID DIFFUSION CONTROL AGENT, CARBOXYLIC ACID SALT AND CARBOXYLIC ACID

(71) Applicant: JSR CORPORATION, Tokyo (JP)

(72) Inventors: Katsuaki Nishikori, Tokyo (JP); Satoshi Okazaki, Tokyo (JP)

(73) Assignee: JSR CORPORATION, Tokyo (JP)

( * ) Notice: Subject to any disclaimer, the term of this patent is extended or adjusted under 35 U.S.C. 154(b) by 264 days.

(21) Appl. No.: 16/552,339

(22) Filed: Aug. 27, 2019

(65) Prior Publication Data

US 2019/0391488 A1    Dec. 26, 2019

Related U.S. Application Data

(63) Continuation of application No. PCT/JP2018/007043, filed on Feb. 26, 2018.

(30) Foreign Application Priority Data

Mar. 1, 2017   (JP) .............................. JP2017-038807

(51) Int. Cl.
| | | |
|---|---|---|
| G03F 7/004 | (2006.01) | |
| C07C 59/105 | (2006.01) | |
| C07C 59/11 | (2006.01) | |
| C07C 59/115 | (2006.01) | |
| C07C 59/13 | (2006.01) | |
| C07C 69/14 | (2006.01) | |
| C07C 381/12 | (2006.01) | |
| C07D 307/00 | (2006.01) | |
| C07D 307/33 | (2006.01) | |
| G03F 7/038 | (2006.01) | |
| G03F 7/039 | (2006.01) | |
| G03F 7/16 | (2006.01) | |
| G03F 7/20 | (2006.01) | |

(Continued)

(52) U.S. Cl.
CPC .......... G03F 7/0045 (2013.01); C07C 59/105 (2013.01); C07C 59/11 (2013.01); C07C 59/115 (2013.01); C07C 59/13 (2013.01); C07C 69/14 (2013.01); C07C 381/12 (2013.01); C07D 307/00 (2013.01); C07D 307/33 (2013.01); G03F 7/038 (2013.01); G03F 7/039 (2013.01); C07C 2601/14 (2017.05); C07C 2603/18 (2017.05); C07C 2603/74 (2017.05); G03F 7/162 (2013.01); G03F 7/168 (2013.01); G03F 7/2006 (2013.01); G03F 7/2041 (2013.01); G03F 7/322 (2013.01); G03F 7/325 (2013.01); G03F 7/38 (2013.01)

(58) Field of Classification Search
CPC ..... C07C 381/12; C07C 59/11; C07C 59/105; C07C 59/115; C07C 59/13; C07C 59/14
See application file for complete search history.

(56) References Cited

U.S. PATENT DOCUMENTS

| | | | |
|---|---|---|---|
| 6,492,091 B2 * | 12/2002 | Kodama | ................. G03F 7/039 430/270.1 |
| 7,781,142 B2 | 8/2010 | Chiba et al. | |
| 8,247,165 B2 | 8/2012 | Kimura et al. | |

(Continued)

FOREIGN PATENT DOCUMENTS

| | | |
|---|---|---|
| CN | 104007623 A | 8/2014 |
| JP | 59-93448 A | 5/1984 |

(Continued)

OTHER PUBLICATIONS

Japanese Office Action dated Aug. 3, 2021 in Japanese Patent Application No. 2019-502989 (with unedited computer generated English translation), 5 pages.

(Continued)

*Primary Examiner* — Amanda C. Walke

(74) *Attorney, Agent, or Firm* — Oblon, McClelland, Maier & Neustadt, L.L.P.

(57) ABSTRACT

A radiation-sensitive resin composition contains: a polymer having an acid-labile group, a radiation-sensitive acid generator, a compound represented by the following formula (1), and a solvent. In the formula (1), X represents an oxygen atom or a sulfur atom; $R^1$ represents a hydrogen atom or a monovalent organic group having 1 to 20 carbon atoms; $R^2$ to $R^5$ each independently represent a hydrogen atom or a monovalent organic group having 1 to 20 carbon atoms, and optionally two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond; $Z^{n+}$ represents a cation having a valency of n; and n is an integer of 1 to 3.

(1)

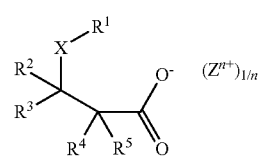

20 Claims, No Drawings

(51) Int. Cl.
*G03F 7/32* (2006.01)
*G03F 7/38* (2006.01)

(56) References Cited

U.S. PATENT DOCUMENTS

| | | | |
|---|---|---|---|
| 8,580,482 | B2 | 11/2013 | Chiba et al. |
| 8,900,802 | B2 | 12/2014 | Allen et al. |
| 9,182,674 | B2 | 11/2015 | Kimura et al. |
| 9,221,742 | B2 * | 12/2015 | Ohashi .................. G03F 7/0045 |
| 10,120,278 | B2 * | 11/2018 | Fukushima ............. G03F 7/162 |
| 2007/0269734 | A1 | 11/2007 | Kimura et al. |
| 2008/0038661 | A1 | 2/2008 | Chiba et al. |
| 2010/0266953 | A1 | 10/2010 | Chiba et al. |
| 2012/0101205 | A1 | 4/2012 | Chiba et al. |
| 2012/0282553 | A1 | 11/2012 | Kimura et al. |
| 2013/0052585 | A1 | 2/2013 | Ayothi et al. |
| 2014/0242526 | A1 | 8/2014 | Allen et al. |
| 2015/0086926 | A1 * | 3/2015 | Ohashi .................. C07C 381/12 430/285.1 |

FOREIGN PATENT DOCUMENTS

| | | | |
|---|---|---|---|
| JP | 6-12452 | A | 1/1994 |
| JP | 11-212265 | A | 8/1999 |
| JP | 2003-5375 | A | 1/2003 |
| JP | 2006-227632 | A | 8/2006 |
| JP | 2008-83370 | A | 4/2008 |
| JP | 2009-134088 | A | 6/2009 |
| JP | 2017-197489 | A | 11/2017 |
| JP | 2018-049264 | A | 3/2018 |
| JP | 2019137684 | A * | 8/2019 |
| WO | WO 2005/069076 | A1 | 7/2005 |
| WO | WO 2006/035790 | A1 | 4/2006 |

OTHER PUBLICATIONS

Combined Taiwanese Office Action and Search Report dated Jun. 28, 2021 in Taiwanese Patent Application No. 107106596 (submitting English translation only), 6 pages.
International Search Report dated May 22, 2018 in PCT/JP2018/007043 (with English translation), 9 pages.
Written Opinion of the International Searching Authority dated May 22, 2018 in PCT/JP2018/007043 (with English translation), 16 pages.
Office Action dated Feb. 15, 2022 in corresponding Japanese Patent Application No. 2019-502989 (with machine-generated whole English translation), 4 pages.

* cited by examiner

RADIATION-SENSITIVE RESIN COMPOSITION, RESIST PATTERN-FORMING METHOD, ACID DIFFUSION CONTROL AGENT, CARBOXYLIC ACID SALT AND CARBOXYLIC ACID

CROSS-REFERENCE TO RELATED APPLICATIONS

The present application is a continuation application of International Application No. PCT/JP2018/007043, filed Feb. 26, 2018, which claims priority to Japanese Patent Application No. 2017-038807, filed Mar. 1, 2017. The contents of these applications are incorporated herein by reference in their entirety.

BACKGROUND OF THE INVENTION

Field of the Invention

The present invention relates to a radiation-sensitive resin composition, a resist pattern-forming method, an acid diffusion control agent, a carboxylic acid salt and a carboxylic acid.

Description of the Related Art

Microfabrication of various types of electronic device structures such as semiconductor devices and liquid crystal devices has been accompanied by demands for further microfabrication of resist patterns in lithography processes. Thus, a variety of radiation-sensitive resin compositions have been studied. Such radiation-sensitive resin compositions contain a component that generates an acid. An exposure of the same generates the acid in light-exposed regions upon irradiation with exposure light such as e.g., a far ultraviolet ray such as an ArF excimer laser, an extreme ultraviolet ray (EUV) or an electron beam to produce a difference in a rate of dissolution in a developer solution between the light-exposed regions and light-unexposed regions through a catalytic action of the acid, thereby allowing a resist pattern to be formed on a substrate.

Such a radiation-sensitive resin composition is required: to achieve superior resolution and rectangularity of the cross-sectional shape of a resist pattern; to be superior in LWR (Line Width Roughness) performance; to be superior in a depth of focus; and to enable a highly accurate pattern to be formed with a high process yield. To address the demands, the structure of the polymer contained in the radiation-sensitive resin composition has been extensively studied. For example, it is known that when a polymer has a lactone structure such as a butyrolactone structure or a norbornanelactone structure, the adhesiveness of the resist pattern to a substrate can be enhanced, and the aforementioned performances can be improved (see Japanese Unexamined Patent Application, Publication Nos. H11-212265, 2003-5375 and 2008-83370).

However, under current circumstances in which miniaturization of resist patterns has proceeded to a level for line widths of no greater than 45 nm, required levels for the aforementioned performances are further elevated.

SUMMARY OF THE INVENTION

According to an aspect of the present invention, a radiation-sensitive resin composition includes: a polymer comprising an acid-labile group; a radiation-sensitive acid generator; a compound represented by formula (1); and a solvent.

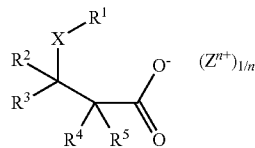

In the formula (1), X represents an oxygen atom or a sulfur atom. $R^1$ represents a hydrogen atom or a monovalent organic group having 1 to 20 carbon atoms. $R^2$ to $R^5$ each independently represent a hydrogen atom or a monovalent organic group having 1 to 20 carbon atoms, and optionally two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond. $Z^{n+}$ represents a cation having a valency of n. n is an integer of 1 to 3.

According to another aspect of the present invention, a resist pattern-forming method includes applying the radiation-sensitive resin composition directly or indirectly on one face of a substrate. The resist film is exposed. The resist film exposed is developed.

According to further aspect of the present invention, an acid diffusion control agent is represented by formula (1').

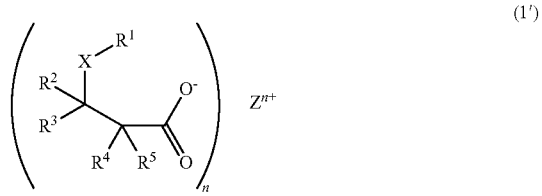

In the formula (1'), X represents an oxygen atom or a sulfur atom. $R^1$ represents a hydrogen atom or a monovalent organic group having 1 to 20 carbon atoms. $R^2$ to $R^5$ each independently represent a hydrogen atom or a monovalent organic group having 1 to 20 carbon atoms, and optionally two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond. $Z^{n+}$ represents a radiation-sensitive cation having a valency of n. n is an integer of 1 to 3.

According to further aspect of the present invention, a carboxylic acid salt is represented by formula (i).

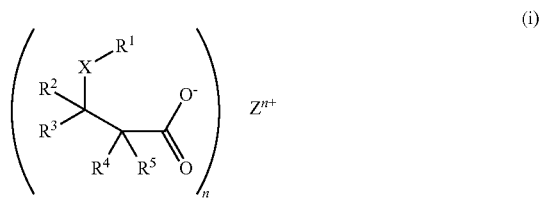

In the formula (i), X represents an oxygen atom or a sulfur atom. $R^1$ represents a hydrogen atom or a monovalent organic group having 1 to 20 carbon atoms. $R^2$ to $R^5$ each independently represent a hydrogen atom or a monovalent organic group having 1 to 20 carbon atoms, and optionally two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond. $Z^{n+}$ represents a radiation-sensitive cation having a valency of n. n is an integer of 1 to 3.

According to further aspect of the present invention, a carboxylic acid is represented by formula (i').

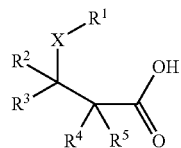

(i')

In the formula (i'), X represents an oxygen atom or a sulfur atom. $R^1$ represents a hydrogen atom or a monovalent organic group having 1 to 20 carbon atoms. $R^2$ and $R^3$ each independently represent a monovalent organic group having 1 to 20 carbon atoms, and $R^4$ and $R^5$ each independently represent a hydrogen atom or a monovalent organic group having 1 to 20 carbon atoms, and optionally two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond.

DESCRIPTION OF EMBODIMENTS

According to one embodiment of the present invention, a radiation-sensitive resin composition comprises: a polymer comprising an acid-labile group, a radiation-sensitive acid generator, a compound represented by the following formula (1), and a solvent.

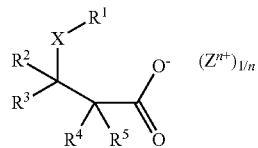

(1)

In the formula (1), X represents an oxygen atom or a sulfur atom; $R^1$ represents a hydrogen atom or a monovalent organic group having 1 to 20 carbon atoms; $R^2$ to $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond; $Z^{n+}$ represents a cation having a valency of n; and n is an integer of 1 to 3.

According to other embodiment of the present invention, a resist pattern-forming method comprises: applying the radiation-sensitive resin composition of the one embodiment directly or indirectly on one face of a substrate; exposing a resist film obtained by the applying; and developing the resist film exposed.

According to other embodiment of the present invention, an acid diffusion control agent is represented by the following formula (1'):

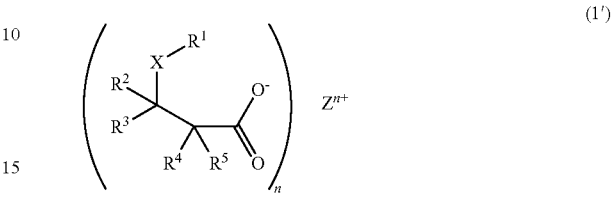

(1')

wherein, in the formula (1'), X represents an oxygen atom or a sulfur atom; $R^1$ represents a hydrogen atom or a monovalent organic group having 1 to 20 carbon atoms; $R^2$ to $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond; $Z^{n+}$ represents a radiation-sensitive cation having a valency of n; and n is an integer of 1 to 3.

According to still other embodiment of the present invention, a carboxylic acid salt is represented by the following formula (i):

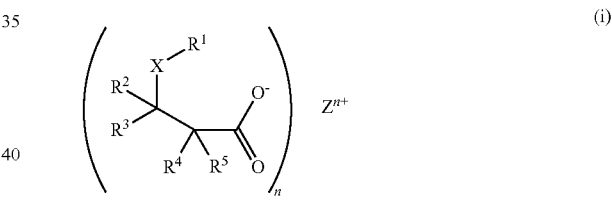

(i)

wherein, in the formula (i), X represents an oxygen atom or a sulfur atom; $R^1$ represents a hydrogen atom or a monovalent organic group having 1 to 20 carbon atoms; $R^2$ to $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond; $Z^{n+}$ represents a radiation-sensitive cation having a valency of n; and n is an integer of 1 to 3.

According to yet other embodiment of the present invention, a carboxylic acid is represented by the following formula (i'):

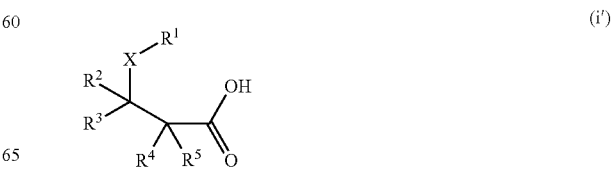

(i')

wherein, in the formula (i'), X represents an oxygen atom or a sulfur atom; $R^1$ represents a hydrogen atom or a monovalent organic group having 1 to 20 carbon atoms; $R^2$ and $R^3$ each independently represent a monovalent organic group having 1 to 20 carbon atoms; $R^4$ and $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond.

The term "organic group" as referred to herein means a group that includes at least one carbon atom. The expression that "a plurality of groups taken together represent an alicyclic structure" as referred to means that a ring constituted taken together is an alicyclic structure. The expression that "a plurality of groups taken together represent an aliphatic heterocyclic structure" as referred to means that a ring constituted taken together is an aliphatic heterocyclic structure. The number of "ring atoms" as referred to means the number of atoms constituting a ring of an alicyclic structure, an cyclic structure, an aliphatic heterocyclic structure or an aromatic heterocyclic structure, and in the case of a polycyclic structure, the number of "ring atoms" means the number of atoms constituting the polyrings.

The radiation-sensitive resin composition and the resist pattern-forming method of the embodiments of the present invention enable a resist pattern with less LWR, higher resolution and superior rectangularity of the cross-sectional shape to be formed while attaining a depth of focus and an inhibitory property of film contraction during post exposure baking (PEB) each being superior. The acid diffusion control agent of the embodiment of the present invention can be suitably used as an acid diffusion control agent component of the radiation-sensitive resin composition. The carboxylic acid salt and the carboxylic acid of the embodiments of the present invention can be suitably used as a basic ingredient of the acid diffusion control agent. Therefore, these can be suitably used for working processes of semiconductor devices, and the like, in which microfabrication is expected to be further in progress hereafter.

Radiation-Sensitive Resin Composition

The radiation-sensitive resin composition of one embodiment of the present invention contains: a polymer having an acid-labile group (hereinafter, may be also referred to as "(A) polymer" or "polymer (A)"); a radiation-sensitive acid generator (hereinafter, may be also referred to as "(B) acid generator" or "acid generator (B)"); a compound represented by the above formula (1) (hereinafter, may be also referred to as "(C) compound" or "compound (C)"); and a solvent (hereinafter, may be also referred to as "solvent (D)" or "(D) solvent").

The radiation-sensitive resin composition may contain as a favorable component, a polymer (hereinafter, may be also referred to as "(E) polymer" or "polymer (E)") having a greater percentage content of fluorine atoms by mass than the polymer (A), and may contain other optional component(s) within a range not leading to impairment of the effects of the present invention.

Due to containing the polymer (A), the acid generating agent (B), the compound (C) and the solvent (D), the radiation-sensitive resin composition is superior in a LWR performance, resolution, rectangularity of the cross-sectional shape, a depth of focus and an inhibitory property of film contraction (hereinafter, these characteristics may be also referred to as "LWR performance, etc." in brief). Although not necessarily clarified and without wishing to be bound by any theory, the reason for achieving the effects described above due to the radiation-sensitive composition having the aforementioned constitution is inferred as in the following, for example. Specifically, with respect to the compound (C), the oxygen atom or sulfur atom represented by X in the formula (1) bonds to a carbon atom adjacent to the carbon atom to which a carboxylate anion group bonds. It is considered that due to thus existing the oxygen atom or sulfur atom at a specific position with respect to the carboxylate anion, for example, the compound (C) has appropriate basicity while maintaining the stability as a carboxylate anion by way of an electronic interaction, etc., whereby a diffusion length of the acid generated from the acid generator (B) is adjusted to be adequately short, consequently leading to the LWR performance, etc., improved. Hereinafter, each component will be described.

(A) Polymer

The polymer (A) is a polymer having an acid-labile group. The "acid-labile group" as referred to means a group that substitutes for a hydrogen atom of a carboxy group, a hydroxy group or the like, and is dissociated by an action of an acid. The polymer (A) typically has the acid-labile group in the structural unit (hereinafter, may be also referred to as "structural unit (I)") that includes the acid-labile group. In addition to the structural unit (I), the polymer (A) preferably has a structural unit (II) that includes a lactone structure, a cyclic carbonate structure, a sultone structure or a combination thereof, and/or a structural unit (III) that includes a hydroxy group, and may also have other structural unit than the structural units (I) to (III). Hereinafter, each structural unit will be described.

Structural Unit (I)

The structural unit (I) includes an acid-labile group.

The structural unit (I) is exemplified by a structural unit represented by the following formula (2) (hereinafter, may be also referred to as "structural unit (I-1)"), a structural unit that includes an acetal structure (hereinafter, may be also referred to as "structural unit (I-2)"), and the like. The polymer (A) may have one, or two or more types of each of the structural unit (I-1) and (I-2). The polymer (A) may have both the structural unit (I-1) and the structural unit (I-2). Hereinafter, the structural unit (I-1) and the structural unit (I-2) will be described.

Structural Unit (I-1)

The structural unit (I-1) is represented by the following formula (2). The group represented by —$CR^{15}R^{16}R^{17}$ in the following formula (2) is the acid-labile group. The acid-labile group is exemplified by: a large protecting group that includes a polycyclic alicyclic structure and has a sterically bulky structure; and a small protecting group that is an acid-labile group other than the large protecting group, and includes an alicyclic structure or does not include a monocyclic alicyclic structure and has a sterically small structure; and the like.

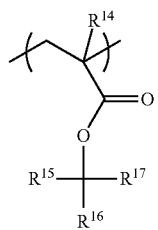

(2)

In the above formula (2), $R^{14}$ represents a hydrogen atom, a fluorine atom, a methyl group or a trifluoromethyl group; $R^{15}$ represents a monovalent hydrocarbon group having 1 to 20 carbon atoms; $R^{16}$ and $R^{17}$ each independently represent a monovalent hydrocarbon group having 1 to 20 carbon atoms, or $R^{16}$ and $R^{17}$ taken together represent an alicyclic structure having 3 to 20 carbon atoms together with the carbon atom to which $R^{16}$ and $R^{17}$ bond.

In light of a degree of copolymerization of a monomer that gives the structural unit (I-1), $R^{14}$ represents preferably a hydrogen atom or a methyl group, and more preferably a methyl group.

The monovalent hydrocarbon group having 1 to 20 carbon atoms which may be represented by $R^{15}$, $R^{16}$ or $R^{17}$ is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:

alkyl groups such as a methyl group, an ethyl group, a n-propyl group and an i-propyl group;

alkenyl groups such as an ethenyl group, a propenyl group and a butenyl group;

alkynyl groups such as an ethynyl group, a propynyl group and a butynyl group; and the like.

Examples of the monovalent alicyclic hydrocarbon group having 3 to 20 carbon atoms include:

monocyclic alicyclic saturated hydrocarbon groups such as a cyclopentyl group and a cyclohexyl group;

monocyclic alicyclic unsaturated hydrocarbon groups such as a cyclopentenyl group and a cyclohexenyl group;

polycyclic alicyclic saturated hydrocarbon groups such as a norbornyl group, an adamantyl group and a tricyclodecyl group;

polycyclic alicyclic unsaturated hydrocarbon groups such as a norbornenyl group and a tricyclodecenyl group; and the like.

Examples of the monovalent aromatic hydrocarbon group having 6 to 20 carbon atoms include:

aryl groups such as a phenyl group, a tolyl group, a xylyl group, a naphthyl group and an anthryl group;

aralkyl groups such as a benzyl group, a phenethyl group, a naphthylmethyl group and an anthryl methyl group; and the like.

Examples of the alicyclic structure having 3 to 20 carbon atoms which may be taken together represented by $R^{16}$ and $R^{17}$ together with the carbon atom to which $R^{16}$ and $R^{17}$ bond include: monocyclic alicyclic structures such as a cyclopropane structure, a cyclobutane structure, a cyclopentane structure, a cyclohexane structure, a cyclopentene structure and a cyclohexene structure; polycyclic alicyclic structures such as a norbornane structure and an adamantane structure; and the like.

Examples of the structural unit (I-1) preferred include structural units represented by the following formulae (2-1) to (2-5) (hereinafter, may be also referred to as "structural units (I-1-1) to (I-1-5)").

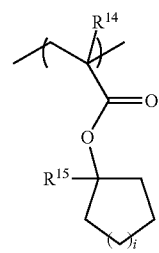

(2-1)

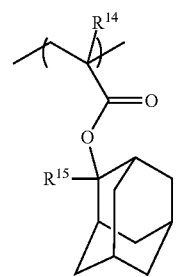

(2-2)

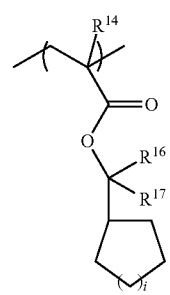

(2-3)

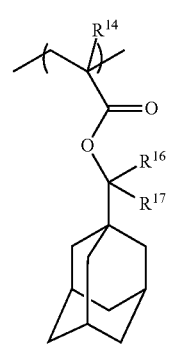

(2-4)

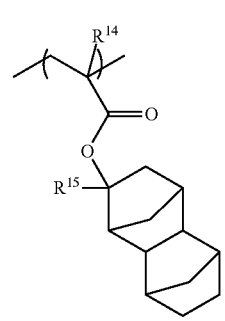

(2-5)

In the above formulae (2-1) to (2-5), $R^{14}$ to $R^{17}$ are as defined in the above formula (2); and i and j are each independently an integer of 1 to 4.

Examples of the structural unit (I-1) include structural units represented by the following formulae, and the like.

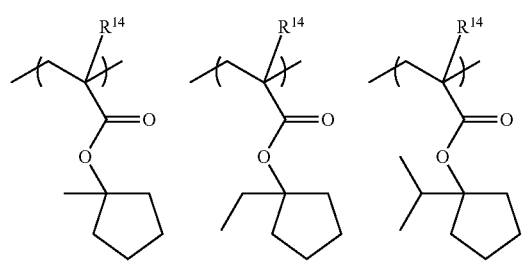
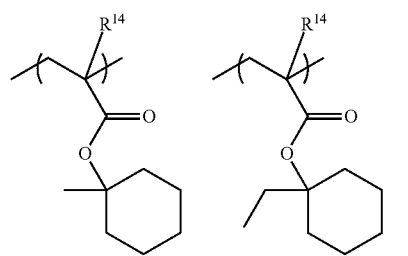
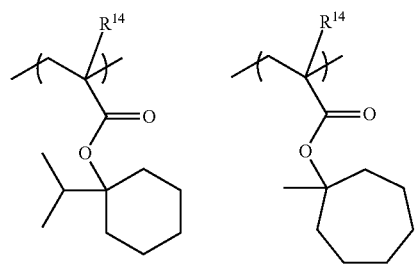
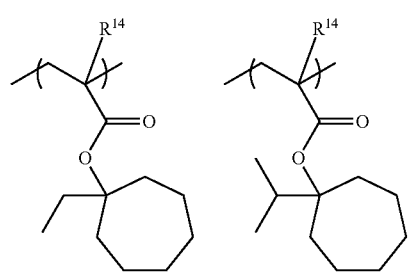
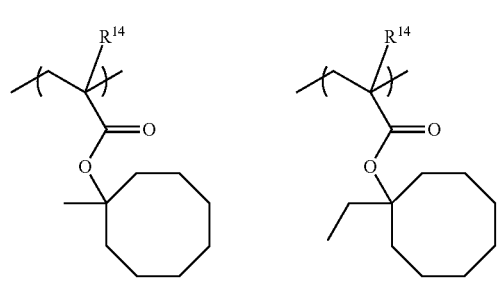
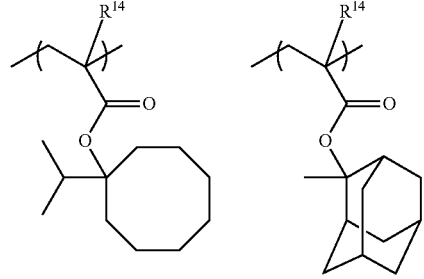
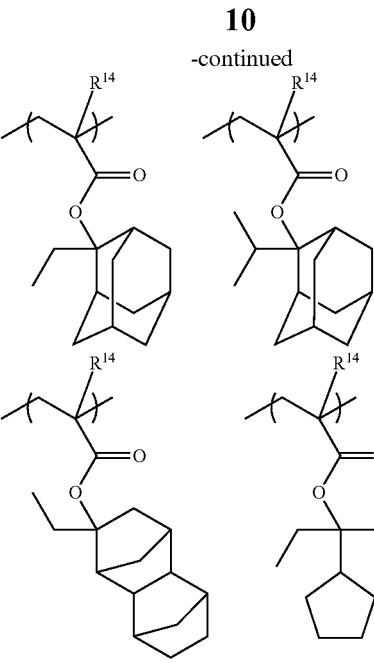
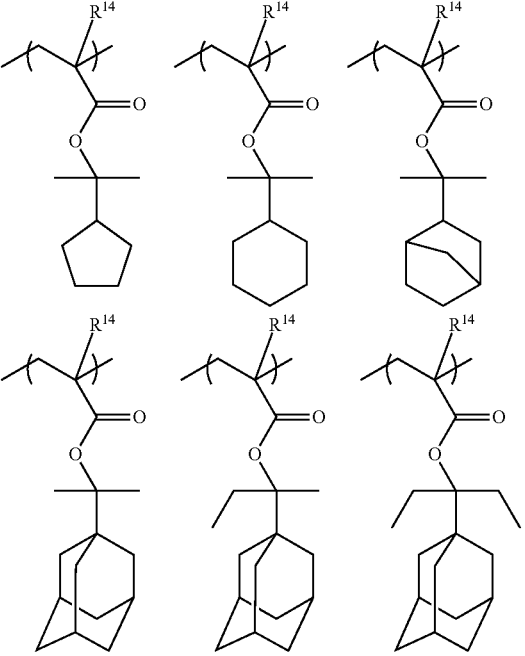

In the above formulae, $R^{14}$ is as defined in the above formula (2).

The structural unit (I-1) is preferably one of the structural units (I-1-1) to (I-1-5), and more preferably a structural unit derived from 1-alkylcyclopentan-1-yl (meth)acrylate, a structural unit derived from 1-alkylcyclohexan-1-yl (meth)acrylate, a structural unit derived from 2-alkyladamantan-2-yl (meth)acrylate, a structural unit derived from 2-(adamantan-1-yl)propan-2-yl (meth)acrylate, a structural unit derived from 2-(cyclohexan-1-yl)propan-2-yl (meth)acrylate, or a structural unit derived from 2-alkyltetracyclododecan-2-yl (meth)acrylate.

Structural Unit (I-2)

The structural unit (I-2) includes an acetal structure. The group that includes an acetal structure is exemplified by a group represented by the following formula (3) (hereinafter, may be also referred to as "group (X)"), and the like. The group (X) is decomposed by an action of the acid to produce *—R$^W$—OH, R$^X$R$^Y$C=O and R$^Z$OH. In the group (X), —C(R$^X$)(R$^Y$)(OR$^Z$) is the acid-labile group.

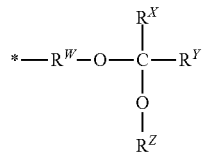
(3)

In the above formula (3), R$^X$ and R$^Y$ each independently represent a hydrogen atom or a monovalent hydrocarbon group having 1 to 20 carbon atoms; R$^Z$ represents a monovalent hydrocarbon group having 1 to 20 carbon atoms; R$^W$ represents a single bond or a divalent hydrocarbon group having 1 to 20 carbon atoms, or two or more of R$^X$, R$^Y$, R$^Z$ and R$^W$ may taken together represent a ring structure having 3 to 20 ring atoms together with the carbon atom or the atom chain to which the two or more of R$^X$, R$^Y$, R$^Z$ and R$^W$ bond; and * denotes a bonding site to a portion other than the group (X) in the structural unit (I-2).

Examples of the monovalent hydrocarbon group having 1 to 20 carbon atoms which may be represented by R$^X$, R$^Y$ or R$^Z$ include groups similar to those exemplified as the monovalent hydrocarbon group having 1 to 20 carbon atoms which may be represented by R$^{15}$, R$^{16}$ or R$^{17}$, and the like.

R$^X$ or R$^Y$ represents preferably a hydrogen atom or a chain hydrocarbon group. The chain hydrocarbon group is preferably an alkyl group, and more preferably a methyl group. R$^Z$ represents preferably an alicyclic hydrocarbon group, more preferably a polycyclic alicyclic saturated hydrocarbon group, and particularly preferably a tetracyclododecan-2-yl group.

R$^W$ represents preferably a single bond or a chain hydrocarbon group, more preferably a single bond or a chain hydrocarbon group, still more preferably a single bond or an alkanediyl group, particularly preferably a single bond or a methanediyl group, and further particularly preferably a single bond.

Examples of the ring structure having 3 to 20 ring atoms taken together represented by two or more of R$^X$, R$^Y$, R$^Z$ and R$^W$ include 1,3-dioxacycloalkane structures such as a 1,3-dioxacyclopentane structure, and the like.

The group (X) is preferably a 1-(tetracyclododecan-2-yloxy)ethan-1-yloxy group.

The lower limit of the proportion of the structural unit (I) contained with respect to the total structural units constituting the polymer (A) is preferably 10 mol %, more preferably 30 mol %, and still more preferably 40 mol %. The upper limit of the proportion of the structural unit (I) is preferably 90 mol %, more preferably 70 mol %, and still more preferably 60 mol %. When the proportion of the structural unit (I) falls within the above range, the sensitivity of the radiation-sensitive resin composition may be further improved, and consequently the LWR performance, etc., may be further improved.

Structural Unit (II)

The structural unit (II) includes a lactone structure, a cyclic carbonate structure, a sultone structure or a combination thereof. When the polymer (A) further has the structural unit (II), solubility in a developer solution can be adjusted, and consequently, the LWR performance, etc. of the radiation-sensitive resin composition can be more improved. Furthermore, adhesiveness of the substrate with the resist pattern formed from the radiation-sensitive resin composition can be improved.

Examples of the structural unit (II) include structural units represented by the following formulae.

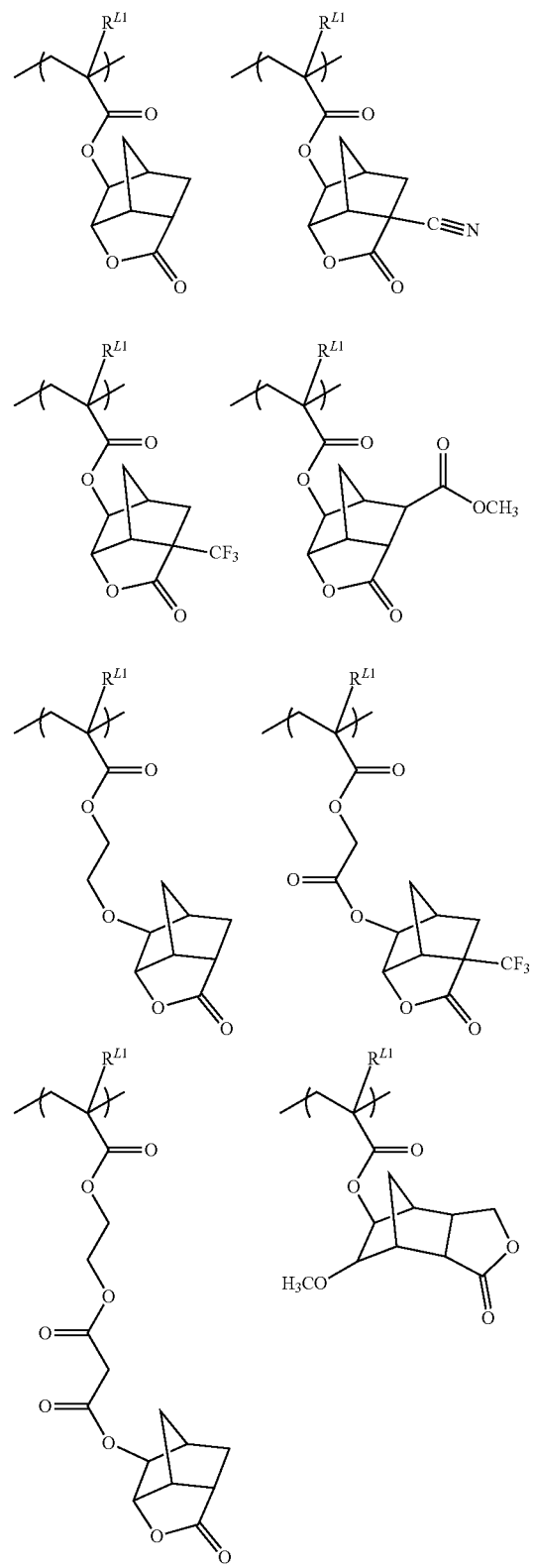

-continued
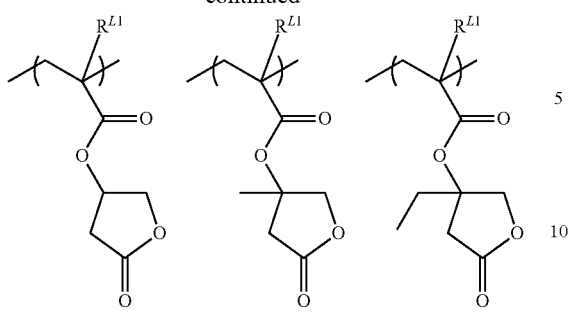
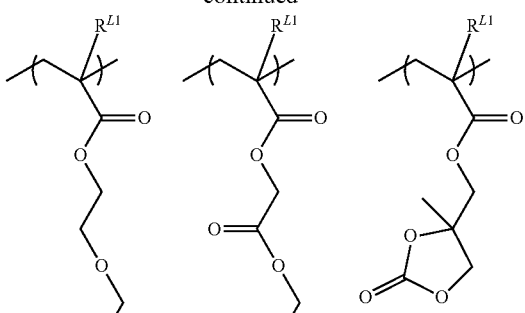
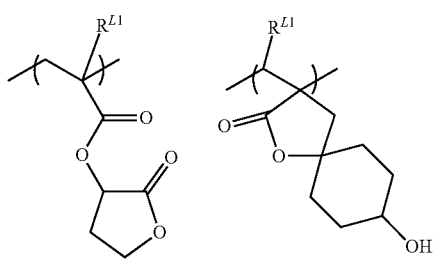
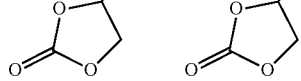
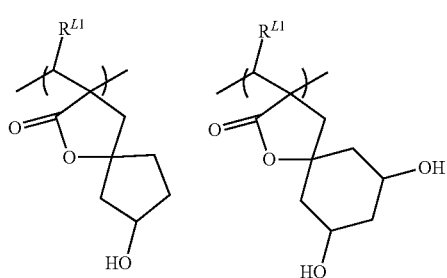
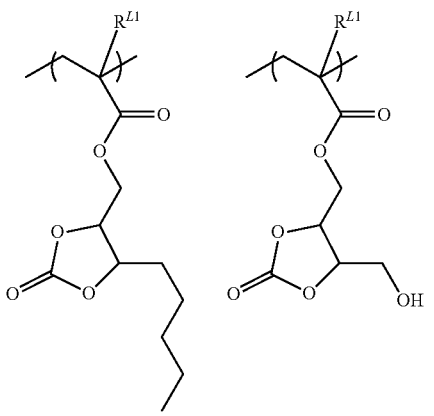
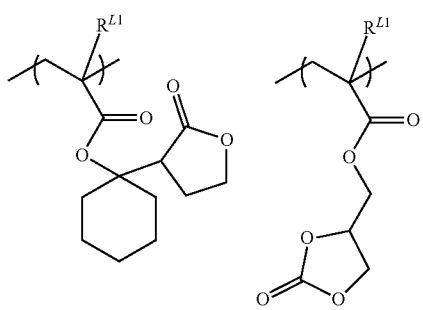
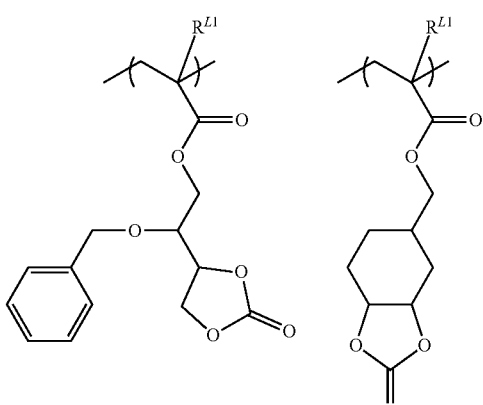
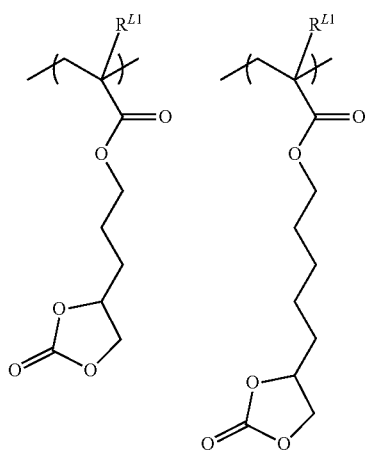
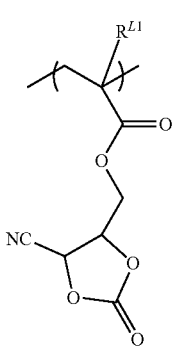
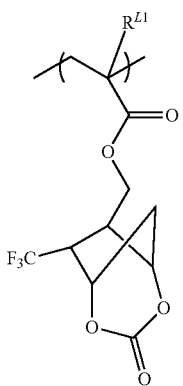

-continued

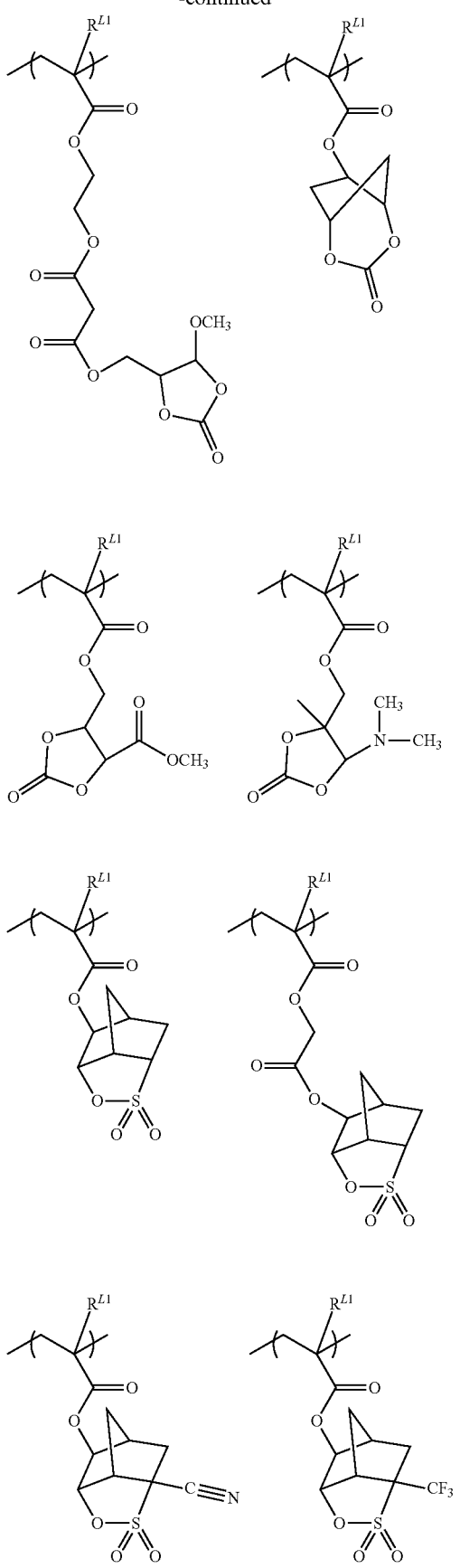
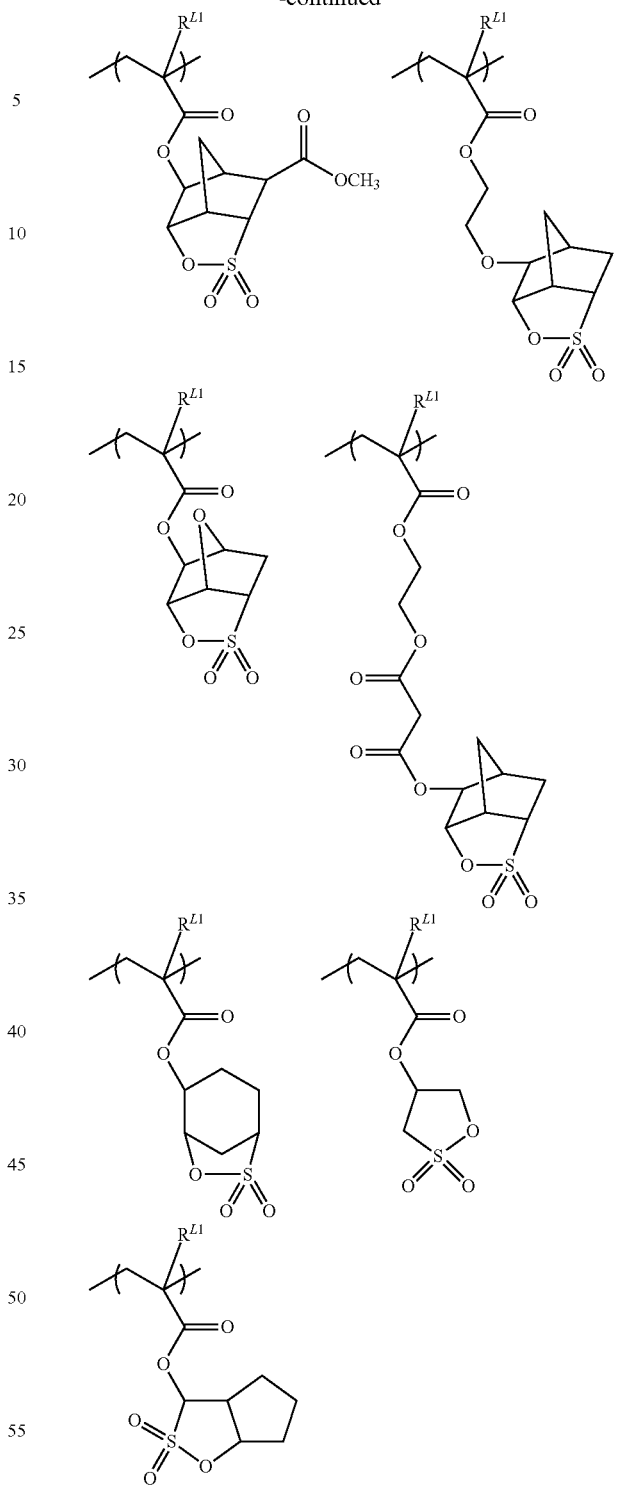

In the above formulae, $R^{L1}$ represents a hydrogen atom, a fluorine atom, a methyl group or a trifluoromethyl group.

Of these, the structural unit (II) is preferably a structural unit that includes a norbornanelactone structure, a structural unit that includes a γ-butyrolactone structure, a structural unit that includes an ethylene carbonate structure, or a structural unit that includes a norbornanesultone structure.

In a case in which the polymer (A) has the structural unit (II), the lower limit of the proportion of the structural unit (II) contained with respect to the total structural units constituting the polymer (A) is preferably 10 mol %, more preferably 30 mol %, and still more preferably 40 mol %. The upper limit of the proportion of the structural unit (II) is preferably 90 mol %, more preferably 70 mol %, and still more preferably 60 mol %. When the proportion of the structural unit (II) falls within the above range, the LWR performance, etc. of the radiation-sensitive resin composition can be further improved. Moreover, adhesiveness of the resist pattern to the substrate can be more improved.

Structural Unit (III)

The structural unit (III) includes a hydroxy group. The hydroxy group is exemplified by an alcoholic hydroxy group, a phenolic hydroxy group, and the like. The polymer (A) is capable of adjusting the solubility in a developer solution when the structural unit (III) is further included, and as a result, the LWR performance, etc. of the radiation-sensitive resin composition can be more improved. In addition, adhesiveness of the resist pattern, which was formed from the radiation-sensitive resin composition, with the substrate can be improved. In a case in which the structural unit (III) includes a phenolic hydroxy group, the sensitivity upon a KrF exposure, an EUV exposure, an electron beam exposure, and the like of the radiation-sensitive resin composition can be more enhanced.

Examples of the structural unit (III) include structural units represented by the following formulae, and the like.

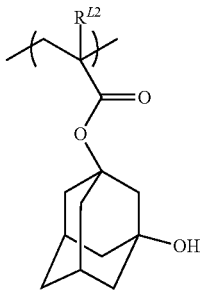
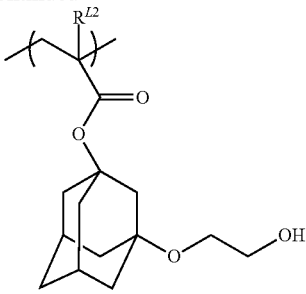
-continued
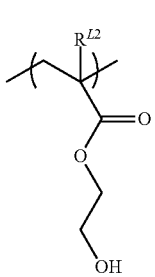
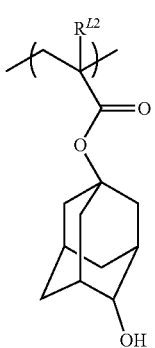
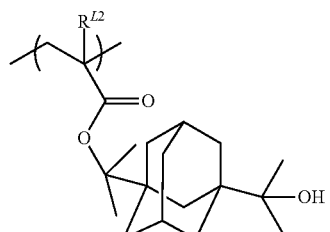
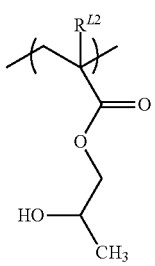
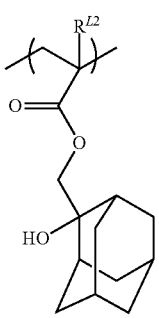
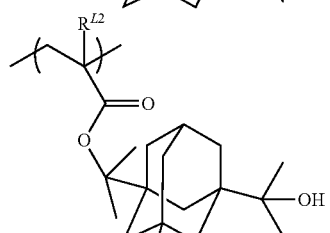
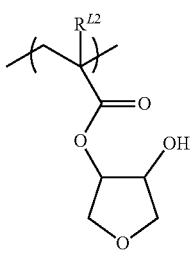
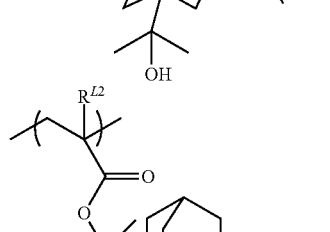
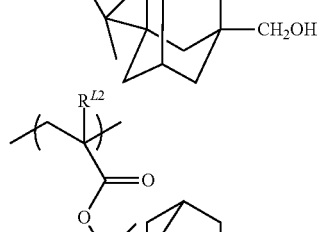
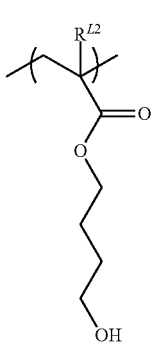
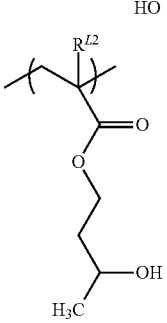
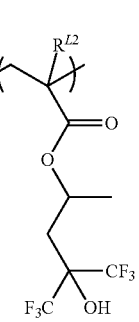

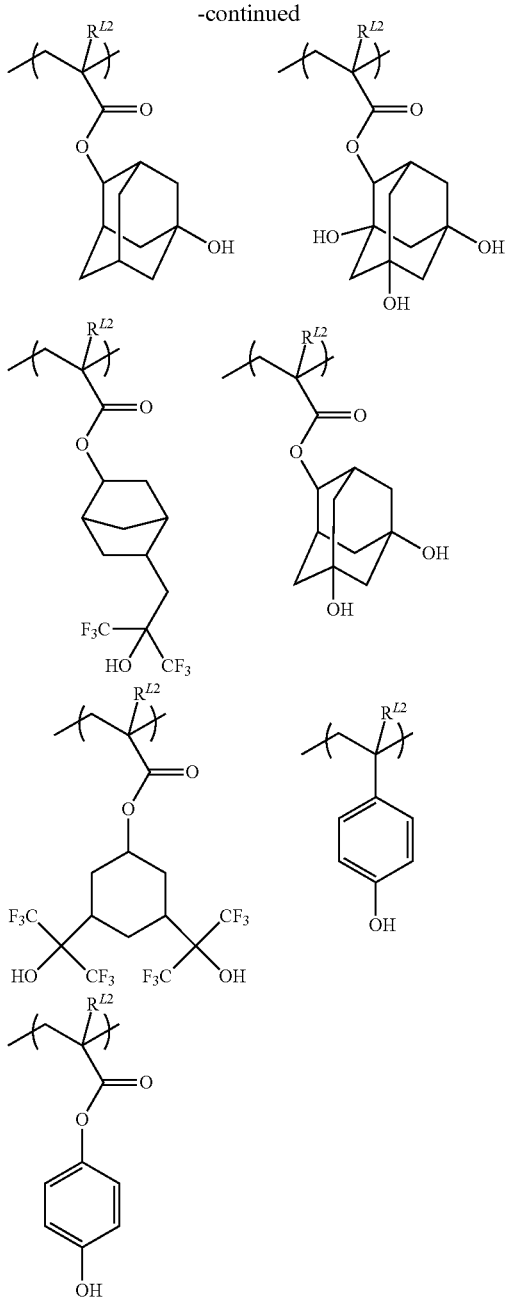

In the above formulae, $R^{L2}$ represents a hydrogen atom, a fluorine atom, a methyl group or a trifluoromethyl group.

The structural unit (III) is preferably a structural unit derived from hydroxystyrene or a structural unit derived from 3-hydroxyadamantan-1-yl (meth)acrylate.

In a case in which the polymer (A) has the structural unit (III), the lower limit of the proportion of the structural unit (III) contained with respect to the total structural units constituting the polymer (A) is preferably 5 mol %, more preferably 30 mol %, and still more preferably 40 mol %. The upper limit of the proportion of the structural unit (III) is preferably 80 mol %, more preferably 70 mol %, and still more preferably 60 mol %.

The structural unit that includes a phenolic hydroxy group may be formed by, e.g., hydrolyzing a polymer obtained by using a monomer, for example, acyloxystyrene such as acetoxystyrene in the presence of a base such as triethylamine.

Other Structural Unit

The polymer (A) may have other structural unit than the structural units (I) to (III). The other structural unit is exemplified by a structural unit that includes a carboxy group, a cyano group, a nitro group, a sulfonamide group or a combination thereof, a structural unit that includes a nondissociable hydrocarbon group, and the like. In a case in which the polymer (A) has the other structural unit, the upper limit of the proportion of the structural unit contained with respect to the total structural units constituting the polymer (A) is preferably 20 mol %, and more preferably 10 mol %.

The lower limit of the content of the polymer (A) with respect to the total solid content of the radiation-sensitive resin composition (sum total of components other than the solvent (D)) is preferably 70% by mass, more preferably 80% by mass, and still more preferably 85% by mass. The upper limit of the content of is preferably 99% by mass, and more preferably 95% by mass. One, or two or more types of the polymer (A) may be contained.

Synthesis Procedure of Polymer (A)

The polymer (A) may be synthesized by, for example, polymerizing a monomer that gives each structural unit by using a radical polymerization initiator or the like in a solvent.

The lower limit of the polystyrene-equivalent weight average molecular weight (Mw) of the polymer (A) as determined by gel permeation chromatography (GPC) is preferably 1,000, more preferably 3,000, still more preferably 4,000, and particularly preferably 5,000. The upper limit of Mw is preferably 50,000, more preferably 30,000, still more preferably 20,000, and particularly preferably 10,000. When Mw of the polymer (A) falls within the above range, coating characteristics of the radiation-sensitive resin composition can be improved, and as a result, the LWR performance, etc. can be more improved.

The upper limit of the ratio (Mw/Mn) of the Mw to the polystyrene equivalent number average molecular weight (Mn) as determined by GPC of the polymer (A) is preferably 5, more preferably 3, still more preferably 2, and particularly preferably 1.6. The lower limit of the ratio is typically 1, and preferably 1.1.

The Mw and the Mn of the polymer as referred to herein are values determined by using gel permeation chromatography (GPC) under the following conditions.

GPC columns: Tosoh Corporation, "G2000 HXL"×2; "G3000 HXL"×1; and "G4000 HXL"×1 column temperature: 40° C.

elution solvent: tetrahydrofuran (Wako Pure Chemical Industries, Ltd.)

flow rate: 1.0 mL/min sample concentration: 1.0% by mass amount of injected sample: 100 μL detector: differential refractometer standard substance: mono-dispersed polystyrene (B) Acid Generator The acid generator (B) is a substance that generates an acid upon an irradiation with a radioactive ray. The acid thus generated allows the acid-labile group included in the polymer (A) or the like to be dissociated, thereby generating a carboxy group, a hydroxy group, etc. As a result, the solubility of the polymer (A) in the developer solution changes, and thus formation of a resist pattern from the radiation-sensitive resin composition is enabled. The acid generator (B) may be contained in the radiation-sensitive resin composition either in the form of a low-molecular-weight compound (hereinafter, may be also referred to as "(B) acid generating agent" or "acid generating agent (B)") or in the form of an acid generator incorporated as a part of the polymer, or may be in both of these forms.

The acid generated from the acid generator (B) may include, for example, sulfonic acid, imidic acid, and the like.

The acid generating agent (B) is exemplified by an onium salt compound, an N-sulfonyloxyimide compound, a sulfonimide compound, a halogen-containing compound, a diazo ketone compound, and the like.

Exemplary onium salt compound includes a sulfonium salt, a tetrahydrothiophenium salt, an iodonium salt, a phosphonium salt, a diazonium salt, a pyridinium salt, and the like.

Specific examples of the acid generating agent (B) include compounds disclosed in paragraphs [0080] to [0113] of Japanese Unexamined Patent Application, Publication No. 2009-134088, and the like.

The acid generating agent (B) is exemplified by a compound represented by the following formula (4).

In the above formula (4), $A^-$ represents a monovalent sulfonic acid anion or a monovalent imidic acid anion; and $T^+$ represents a radiation-sensitive monovalent onium cation.

The acid generating agent (B) that generates sulfonic acid upon irradiation with a radioactive ray is exemplified by a compound represented by the following formula (4-1) (hereinafter, may be also referred to as "compound (4-1)"), and the like. When the acid generating agent (B1) has the following structure, it is expected that a diffusion length of the acid generated upon the exposure in the resist film will be more properly reduced through e.g., an interaction with the structural unit (I) of the polymer (A) or the like, and as a result, the LWR performance, etc. of the radiation-sensitive resin composition can be more improved.

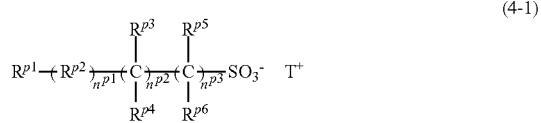

In the above formula (4-1), $R^{p1}$ represents a monovalent group that includes a ring structure having no less than 5 ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10; $n^{p2}$ is an integer of 0 to 10; $n^{p3}$ is an integer of 0 to 10, wherein $(n^{p1}+n^{p2}+n^{p3})$ is no less than 1 and no greater than 30, and in a case in which $n^{p1}$ is no less than 2, a plurality of $R^{p2}$s may be identical or different, in a case in which $n^{p2}$ is no less than 2, a plurality of $R^{p3}$s may be identical or different, and a plurality of $R^{p4}$s may be identical or different, and in a case in which $n^{p3}$ is no less than 2, a plurality of $R^{p5}$s may be identical or different, and a plurality of $R^{p6}$s may be identical or different; and $T^+$ represents a radiation-sensitive monovalent onium cation.

The monovalent group that includes a ring structure having 5 or more ring atoms which is represented by $R^{p1}$ is exemplified by: a monovalent group that includes an alicyclic structure having 5 or more ring atoms; a monovalent group that includes an aliphatic heterocyclic structure having 5 or more ring atoms; a monovalent group that includes an cyclic structure having 5 or more ring atoms; a monovalent group that includes an aromatic heterocyclic structure having 5 or more ring atoms; and the like.

Examples of the alicyclic structure having no less than 5 ring atoms include:

monocyclic saturated alicyclic structures such as a cyclopentane structure, a cyclohexane structure, a cycloheptane structure, a cyclooctane structure, a cyclononane structure, a cyclodecane structure and a cyclododecane structure;

monocyclic unsaturated alicyclic structures such as a cyclopentene structure, a cyclohexene structure, a cycloheptene structure, a cyclooctene structure and a cyclodecene structure;

polycyclic saturated alicyclic structures such as a norbornane structure, an adamantane structure, a tricyclodecane structure and a tetracyclododecane structure;

polycyclic unsaturated alicyclic structures such as a norbornene structure and a tricyclodecene structure; and the like.

Examples of the aliphatic heterocyclic structure having 5 or more ring atoms include:

lactone structures such as a hexanolactone structure and a norbornanelactone structure;

sultone structures such as a hexanosultone structure and a norbornanesultone structure;

oxygen atom-containing heterocyclic structures such as an oxacycloheptane structure and an oxanorbornane structure;

nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the cyclic structure having 5 or more ring atoms include a benzene structure, a naphthalene structure, a phenanthrene structure, an anthracene structure, and the like.

Examples of the aromatic heterocyclic structure having 5 or more ring atoms include:

oxygen atom-containing heterocyclic structures such as a furan structure, a pyran structure, a benzofuran structure and a benzopyran structure;

nitrogen atom-containing heterocyclic structures such as a pyridine structure, a pyrimidine structure and an indole structure; and the like.

The lower limit of the number of ring atoms of the ring structure included in $R^{p1}$ is preferably 6, more preferably 8, still more preferably 9, and particularly preferably 10. The upper limit of the number of ring atoms is preferably 15, more preferably 14, still more preferably 13, and particularly preferably 12. When the number of ring atoms falls within the above range, the aforementioned diffusion length of the acid may be further properly reduced, and as a result, the LWR performance, etc. of the radiation-sensitive resin composition can be more improved.

A part or all of hydrogen atoms included in the ring structure of $R^{p1}$ may be substituted with a substituent. Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, the hydroxy group is preferred.

$R^{p1}$ represents preferably a monovalent group that includes an alicyclic structure having 5 or more ring atoms or a monovalent group that includes an aliphatic heterocyclic structure having 5 or more ring atoms, more preferably a monovalent group that includes an alicyclic structure having 9 or more ring atoms or a monovalent group that includes an aliphatic heterocyclic structure having 9 or more ring atoms, still more preferably an adamantyl group, a hydroxyadamantyl group, a norbornanelactone-yl group, a norbornanesultone-yl group and a 5-oxo-4-oxatricyclo[4.3.1.1$^{3,8}$]undecan-yl group, and particularly preferably an adamantyl group.

Examples of the divalent linking group represented by $R^{p2}$ include a carbonyl group, an ether group, a carbonyloxy group, a sulfide group, a thiocarbonyl group, a sulfonyl group, a divalent hydrocarbon group and the like. Of these, a carbonyloxy group, a sulfonyl group, an alkanediyl group or a divalent alicyclic saturated hydrocarbon group is preferred, a carbonyloxy group or a divalent alicyclic saturated hydrocarbon group is more preferred, a carbonyloxy group or a norbornanediyl group is still more preferred, and a carbonyloxy group is particularly preferred.

The monovalent hydrocarbon group having 1 to 20 carbon atoms which may be represented by $R^{p3}$ or $R^{p4}$ is exemplified by an alkyl group having 1 to 20 carbon atoms and the like; the monovalent fluorinated hydrocarbon group having 1 to 20 carbon atoms which may be represented by $R^{p3}$ or $R^{p4}$ is exemplified by a fluorinated alkyl group having 1 to 20 carbon atoms and the like; $R^{p3}$ or $R^{p4}$ independently represent preferably a hydrogen atom, a fluorine atom or a fluorinated alkyl group, more preferably a fluorine atom or a perfluoroalkyl group, and still more preferably a fluorine atom or a trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms and the like; $R^{p5}$ or $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

In the above formula, $n^{p1}$ is preferably an integer of 0 to 5, more preferably an integer of 0 to 3, still more preferably an integer of 0 to 2, and particularly preferably 0 or 1.

In the above formula, $n^{p2}$ is preferably an integer of 0 to 5, more preferably an integer of 0 to 2, still more preferably 0 or 1, and particularly preferably 0.

The lower limit of $n^{p3}$ is preferably 1, and more preferably 2. When $n^{p3}$ is no less than 1, the strength of the acid generated from the compound (4-1) can be increased, and consequently, the radiation-sensitive resin composition enables the LWR performance, etc. to be more improved. The upper limit of $n^{p3}$ is preferably 4, more preferably 3, and still more preferably 2.

The lower limit of ($n^{p1}+n^{p2}+n^{p3}$) is preferably 2, and more preferably 4. The upper limit of ($n^{p1}+n^{p2}+n^{p3}$) is preferably 20, and more preferably 10.

Examples of the radiation-sensitive monovalent onium cation represented by T$^+$ include: a cation represented by the following formula (r-a) (hereinafter, may be also referred to as "cation (r-a)"), a cation represented by the following formula (r-b) (hereinafter, may be also referred to as "cation (r-b)"), a cation represented by the following formula (r-c) (hereinafter, may be also referred to as "cation (r-c)"), and the like.

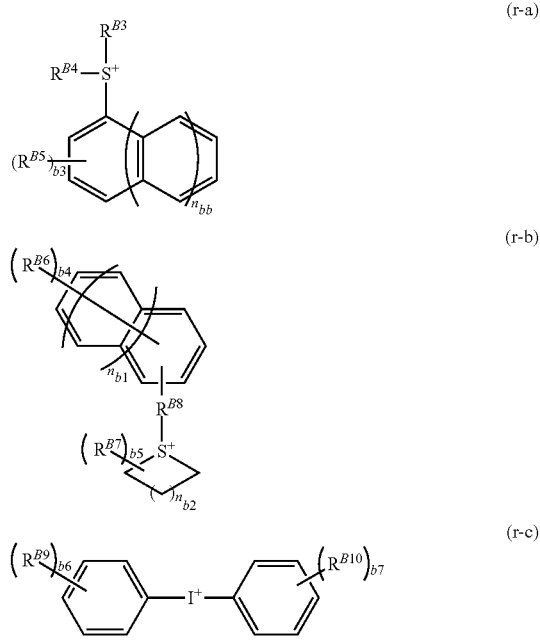

In the above formula (r-a), $R^{B3}$ and $R^{B4}$ each independently represent a monovalent organic group having 1 to 20 carbon atoms; $R^{B5}$ represents a monovalent organic group having 1 to 20 carbon atoms, a hydroxy group, a nitro group or a halogen atom; b3 is each independently an integer of 0 to 5, wherein in a case in which there exists a plurality of $R^{B5}$s, the plurality of $R^{B5}$s may be identical or different, and the plurality of $R^{B5}$ may taken together represent a ring structure; and $n_{bh}$ is an integer of 0 to 3.

The monovalent organic group having 1 to 20 carbon atoms which may be represented by $R^{B3}$, $R^{B4}$ or $R^{B5}$ exemplified by: a monovalent hydrocarbon group having 1 to 20 carbon atoms; a monovalent group (g) that includes a divalent hetero atom-containing group between two adjacent carbon atoms of the monovalent hydrocarbon group, or at the end of the atomic bonding side of the monovalent hydrocarbon group; a monovalent group obtained from the monovalent hydrocarbon group or the group (g) by substituting with a monovalent hetero atom-containing group a part or all of hydrogen atoms included therein; and the like.

$R^{B3}$ or $R^{B4}$ represents preferably a monovalent unsubstituted hydrocarbon group or a hydrocarbon group having 1 to 20 carbon atoms obtained therefrom by substituting a hydrogen atom included therein with a substituent, more preferably a monovalent unsubstituted aromatic hydrocarbon group having 6 to 18 carbon atoms or an aromatic hydrocarbon group obtained therefrom by substituting a hydrogen atom included therein with a substituent, and still more preferably a phenyl group.

The substituent which may substitute for the hydrogen atom included in the monovalent hydrocarbon group having 1 to 20 carbon atoms which may be represented by $R^{B3}$ or $R^{B4}$ is preferably a substituted or unsubstituted monovalent hydrocarbon group having 1 to 20 carbon atoms, —OSO$_2$—$R^k$, —SO$_2$—$R^k$, —OR$^k$, —COOR$^k$, —O—CO—R$^k$, —O—R$^{kk}$—COOR$^k$, —R$^{kk}$—CO—R$^k$ or —S—R$^k$, wherein R$^k$ represents a monovalent hydrocarbon group having 1 to 10 carbon atoms; and $R^{kk}$ represents a single bond or a divalent hydrocarbon group having 1 to 10 carbon atoms.

$R^{B5}$ represents preferably a substituted or unsubstituted monovalent hydrocarbon group having 1 to 20 carbon atoms, —$OSO_2$—$R^k$, —$SO_2$—$R^k$, —$OR^k$, —$COOR^k$, —O—CO—$R^k$, —O—$R^{kk}$—$COOR^k$, —$R^{kk}$—CO—$R^k$ or —S—$R^k$, wherein $R^k$ represents a monovalent hydrocarbon group having 1 to 10 carbon atoms; and $R^{kk}$ represents a single bond or a divalent hydrocarbon group having 1 to 10 carbon atoms.

In the above formula (r-b), $R^{B6}$ and $R^{B7}$ each independently represent a monovalent organic group having 1 to 20 carbon atoms, a hydroxy group, a nitro group or a halogen atom; b4 is an integer of 0 to 7, wherein in a case in which there exists a plurality of $R^{B6}$s, the plurality of $R^{B6}$s may be identical or different, and the plurality of $R^{B6}$s may taken together represent a ring structure; b5 is an integer of 0 to 6, wherein in a case in which there exists a plurality of $R^{B7}$s, the plurality of $R^{B7}$s may be identical or different, and the plurality of $R^{B7}$ may taken together represent a ring structure; $n_{b2}$ is an integer of 0 to 3; $R^{B8}$ represents a single bond or divalent organic group having 1 to 20 carbon atoms; and $n_{b1}$ is an integer of 0 to 2.

$R^{B6}$ or $R^{B7}$ represents preferably a substituted or unsubstituted monovalent hydrocarbon group having 1 to 20 carbon atoms, —$OR^k$, —$COOR^k$, —O—CO—$R^k$, —O—$R^{kk}$—$COOR^k$ or —$R^{kk}$—CO—$R^k$, wherein $R^k$ represents a monovalent hydrocarbon group having 1 to 10 carbon atoms; and $R^{kk}$ represents a single bond or a divalent hydrocarbon group having 1 to 10 carbon atoms.

In the above formula (r-c), $R^{B9}$ and $R^{B10}$ each independently represent a monovalent organic group having 1 to 20 carbon atoms, a hydroxy group, a nitro group or a halogen atom; and b6 and b7 are each independently an integer of 0 to 5, wherein in a case in which there exists a plurality of $R^{B9}$s, the plurality of $R^{B9}$s may be identical or different, and the plurality of $R^{B9}$s may taken together represent a ring structure, and in a case in which there exists a plurality of $R^{B10}$s, the plurality of $R^{B10}$s may be identical or different, and the plurality of $R^{B10}$s may taken together represent a ring structure.

$R^{B9}$ or $R^{B10}$ represents preferably a substituted or unsubstituted monovalent hydrocarbon group having 1 to 20 carbon atoms, —$OSO_2$—$R^k$, —$SO_2$—$R^k$, —$OR^k$, —CO-$OR^k$, —O—CO—$R^k$, —O—$R^{kk}$—$COOR^k$, —$R^{kk}$—CO—$R^k$, —S—$R^k$, or a ring structure taken together represented by two or more of $R^{B9}$ and $R^{B10}$, wherein $R^k$ represents a monovalent hydrocarbon group having 1 to 10 carbon atoms; and $R^{kk}$ represents a single bond or a divalent hydrocarbon group having 1 to 10 carbon atoms.

Examples of the monovalent hydrocarbon group having 1 to 20 carbon atoms which may be represented by $R^{B5}$, $R^{B6}$, $R^{B7}$, $R^{B9}$ or $R^{B10}$ include:

linear alkyl groups such as a methyl group, an ethyl group, a n-propyl group and a n-butyl group;

branched alkyl groups such as an i-propyl group, an i-butyl group, a sec-butyl group and a t-butyl group;

aryl groups such as a phenyl group, a tolyl group, a xylyl group, a mesityl group and a naphthyl group;

aralkyl groups such as a benzyl group and a phenethyl group; and the like.

Examples of the divalent organic group represented by $R^{B8}$ include groups obtained by removing one hydrogen atom from the monovalent organic group having 1 to 20 carbon atoms exemplified as $R^{B3}$, $R^{B4}$ and $R^{B5}$ in the above formula (r-a), and the like.

Examples of the substituent which may substitute for the hydrogen atom included in the hydrocarbon group which may be represented by $R^{B5}$, $R^{B6}$, $R^{B7}$, $R^{B9}$ or $R^{B10}$ include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, the halogen atom is preferred, and a fluorine atom is more preferred.

$R^{B5}$, $R^{B6}$, $R^{B7}$, $R^{B9}$ or $R^{B10}$ represents preferably an unsubstituted linear or branched monovalent alkyl group, a monovalent fluorinated alkyl group, an unsubstituted monovalent aromatic hydrocarbon group, —$OSO_2$—$R^k$ or —$SO_2$—$R^k$, more preferably a fluorinated alkyl group or an unsubstituted monovalent aromatic hydrocarbon group, and still more preferably a fluorinated alkyl group.

In the formula (r-a), b3 is preferably an integer of 0 to 2, more preferably 0 or 1, and still more preferably 0; $n_{bb}$ is preferably 0 or 1, and more preferably 0. In the formula (r-b), b4 is preferably an integer of 0 to 2, more preferably 0 or 1, and still more preferably 0; b5 is preferably an integer of 0 to 2, more preferably 0 or 1, and still more preferably 0; $n_{b2}$ is preferably 2 or 3, more preferably 2; and $n_{b1}$ is preferably 0 or 1, and more preferably 0. In the formula (r-c), b6 or b7 is preferably an integer of 0 to 2, more preferably 0 or 1, and still more preferably 0.

Of these, t represents preferably the cation (r-a), and more preferably a triphenylsulfonium cation.

Examples of the acid generating agent (B) include: as an acid generating agent that generates sulfonic acid, compounds represented by the following formulae (4-1-1) to (4-1-18) (hereinafter, may be also referred to as "compounds (4-1-1) to (4-1-18)"); as an acid generating agent that generates imidic acid, compounds represented by the following formulae (4-2-1) to (4-2-3) (hereinafter, may be also referred to as "compounds (4-2-1) to (4-2-3)"), and the like.

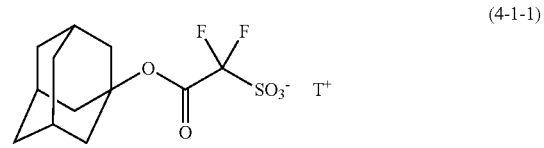

(4-1-1)

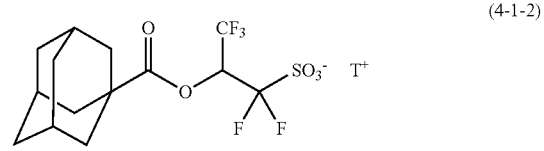

(4-1-2)

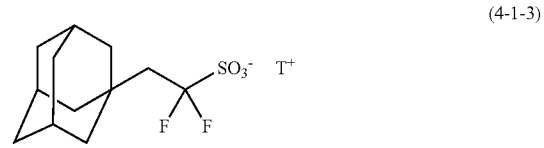

(4-1-3)

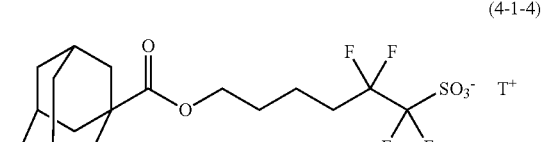

(4-1-4)

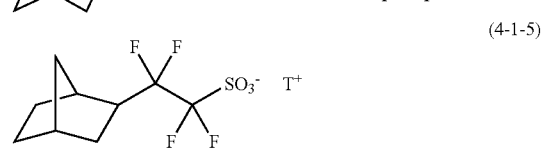

(4-1-5)

(4-1-6)
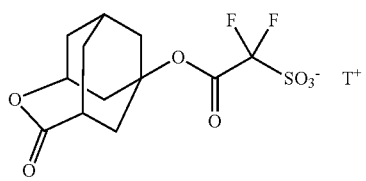
(4-1-7)
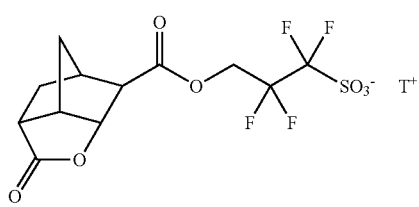
(4-1-8)
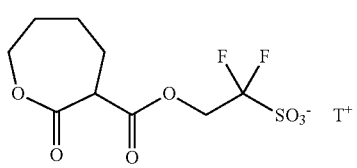
(4-1-9)
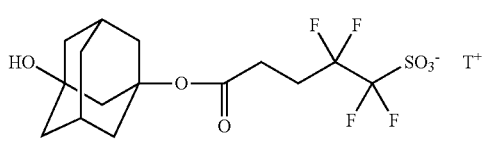
(4-1-10)
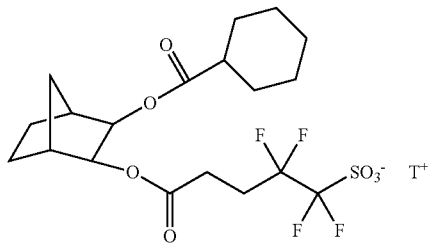
(4-1-11)
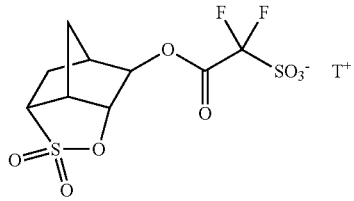
(4-1-12)
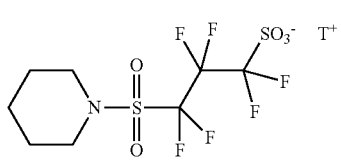
(4-1-13)
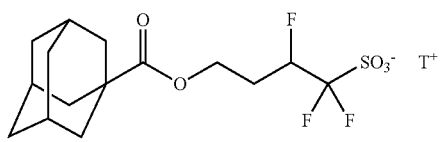
(4-1-14)
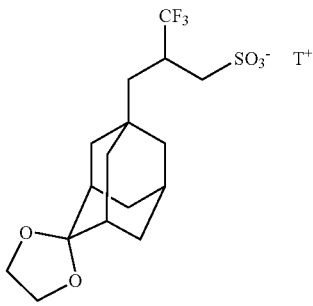
(4-1-15)
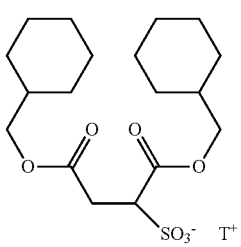
(4-1-16)
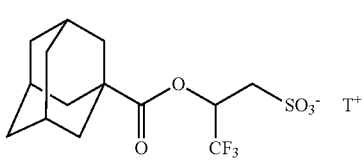
(4-1-17)
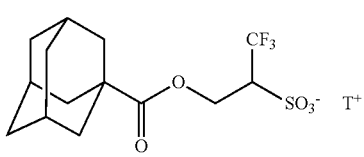
(4-1-18)
(4-2-1)
(4-2-2)
(4-2-3)
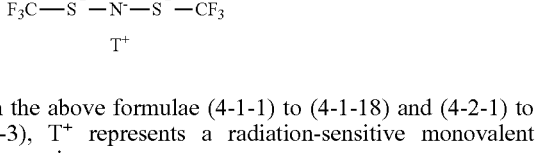
In the above formulae (4-1-1) to (4-1-18) and (4-2-1) to (4-2-3), $T^+$ represents a radiation-sensitive monovalent onium cation.
As the acid generating agent (B), compounds (4-1-1) to (4-1-4) and (4-1-16) to (4-1-18), and a compound (4-2-1) are preferred.
In a case in which the acid generator (B) is the acid generating agent (B), the lower limit of the content of the acid generating agent (B) with respect to 100 parts by mass of the polymer (A) is preferably 0.1 parts by mass, more preferably 1 part by mass, still more preferably 5 parts by mass, and particularly preferably 10 parts by mass. The upper limit of the content of the acid generating agent (B) is preferably 50 parts by mass, more preferably 40 parts by mass, still more preferably 30 parts by mass, and particularly preferably 25 parts by mass. When the content of the acid generating agent (B) falls within the above range, the sensitivity and developability of the radiation-sensitive resin composition may be improved, and consequently, the LWR performance, etc., may be more improved. One, or two or more types of the acid generator (B) may be contained.

(C) Compound

The compound (C) is represented by the following formula (1).

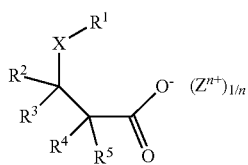

(1)

In the above formula (1), X represents an oxygen atom or a sulfur atom; $R^1$ represents a hydrogen atom or a monovalent organic group having 1 to 20 carbon atoms; $R^2$ to $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond; $Z^{n+}$ represents a cation having a valency of n; and n is an integer of 1 to 3.

The monovalent organic group having 1 to 20 carbon atoms which may be represented by $R^1$ to $R^5$ is exemplified by: a monovalent hydrocarbon group having 1 to 20 carbon atoms; a group (α) that includes a divalent hetero atom-containing group between two adjacent carbon atoms of the monovalent hydrocarbon group, or at the end of the atomic bonding side of the monovalent hydrocarbon group; a group obtained from the monovalent hydrocarbon group or the group (α) by substituting with a monovalent hetero atom-containing group a part or all of hydrogen atoms included therein; and the like.

Examples of the monovalent hydrocarbon group having 1 to 20 carbon atoms include groups similar to those exemplified as the monovalent hydrocarbon group having 1 to 20 carbon atoms which may be represented by $R^{15}$, $R^{16}$ or $R^{17}$ in the above formula (2), and the like.

Examples of the hetero atom constituting the monovalent or divalent hetero atom-containing group include an oxygen atom, a nitrogen atom, a sulfur atom, a phosphorus atom, a silicon atom, a halogen atom, and the like. Examples of the halogen atom include a fluorine atom, a chlorine atom, a bromine atom, an iodine atom, and the like.

Examples of the divalent hetero atom-containing group include —O—, —CO—, —S—, —CS—, —NR'—, groups obtained by combining two or more of the same, and the like, wherein R' represents a hydrogen atom or a monovalent hydrocarbon group. Of these, —CO— is preferred.

Examples of the monovalent hetero atom-containing group include: halogen atoms such as a fluorine atom, a chlorine atom, a bromine atom and an iodine atom; a hydroxy group, a carboxy group, a cyano group, an amino group, a sulfanyl group, and the like. Of these, a fluorine atom is preferred.

Examples of the alicyclic structure having 3 to 20 ring atoms taken together represented by two or more of $R^2$ to $R^5$ together with the carbon atom to which the two or more of $R^2$ to $R^5$ bond include a cyclopropane structure, a cyclobutane structure, a cyclopentane structure, a cyclohexane structure, a cyclopentene structure, a cyclohexene structure, a norbornane structure, an adamantane structure, a fluorene structure, and the like. Of these, a cyclohexane structure, an adamantane structure or fluorene structure is preferred.

Examples of the aliphatic heterocyclic structure having 3 to 20 ring atoms taken together represented by two or more of $R^2$ to $R^5$ together with the carbon atom to which the two or more of $R^2$ to $R^5$ bond include a lactone structure, a cyclic carbonate structure, a sultone structure, an oxacycloalkane structure, an azacycloalkane structure, a thiacycloalkane structure, and the like. Of these, a lactone structure is preferred, and a butyrolactone structure or a norbornanelactone structure is more preferred.

The monovalent organic group which may be represented by $R^1$ is preferably the hydrocarbon group or the group that includes a divalent hetero atom-containing group at the end of the atomic bonding side of the hydrocarbon group, more preferably the chain hydrocarbon group or the group that includes —CO— at the end of the atomic bonding side of the chain hydrocarbon group, still more preferably the alkyl group or the alkylcarbonyl group, and particularly preferably a methyl group or an acetyl group.

$R^1$ represents preferably a hydrogen atom, in light of the LWR performance.

$R^2$ or $R^3$ represents preferably a hydrogen atom or a substituted or unsubstituted hydrocarbon group, or a group that includes an aliphatic heterocyclic structure, more preferably a hydrogen atom, a hydrocarbon group, a hydroxy group-substituted hydrocarbon group, a hydroxy group, a fluorine atom-substituted hydrocarbon group, or a group that includes a lactone structure, and still more preferably a methyl group, a cyclohexyl group, a naphthyl group, a butyrolactone-yl group, a hydroxydi(trifluoromethyl)ethyl group, a hydroxydimethyl ethyl group or a hydrogen atom.

$R^4$ or $R^5$ represents preferably a hydrogen atom.

The cation having a valency of n represented by $Z^{n+}$ is exemplified by:

a monovalent onium cation, an alkali metal cation or the like as a monovalent cation;

a divalent onium cation, an alkaline earth metal cation or the like as a divalent cation;

a trivalent onium cation, a trivalent metal cation or the like as a trivalent cation; and the like. The onium cation may be either radiation-sensitive, or radiation-insensitive. Examples of the radiation-sensitive onium cation include such cations as exemplified as the radiation-sensitive monovalent onium cation represented by $T^+$ in the formula (4) for the aforementioned acid generating agent (B), i.e., a sulfonium cation, an iodonium cation, a tetrahydrothiophenium cation and the like. The divalent or trivalent cation may be exemplified by both a cation having a cation moiety of either +2 or +3 charge, and a cation that includes two or three cation moieties each having +1 charge.

In the above formula, n is preferably 1 or 2, and more preferably 1.

$Z^{n+}$ represents preferably an onium cation, more preferably a monovalent or divalent sulfonium cation, still more preferably a monovalent sulfonium cation, and particularly preferably a triphenylsulfonium cation.

Examples of the compound (C) include compounds represented by the following formulae (1-1) to (1-16) (hereinafter, may be also referred to as "compounds (1-1) to (1-16)"), and the like.
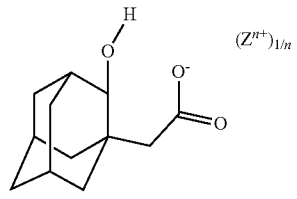
(1-1)
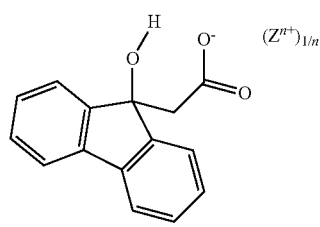
(1-2)
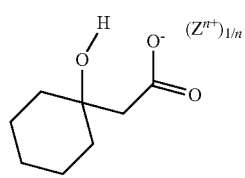
(1-3)
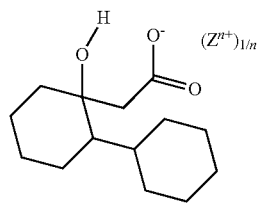
(1-4)
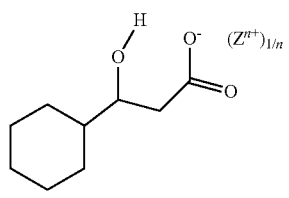
(1-5)
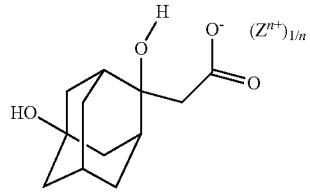
(1-6)
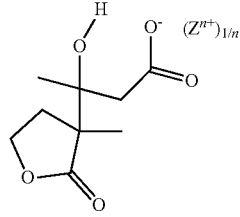
(1-7)
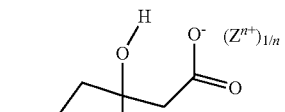
(1-8)
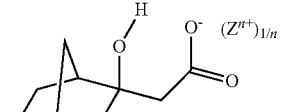
(1-9)
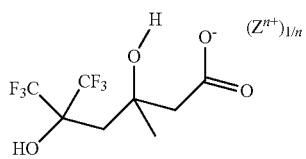
(1-10)
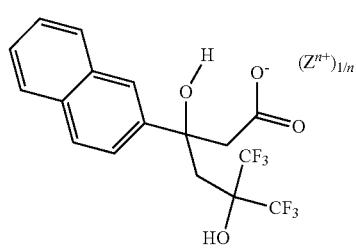
(1-11)
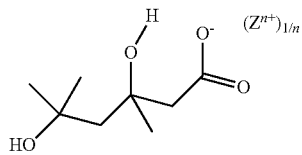
(1-12)
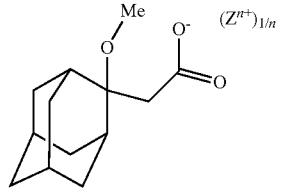
(1-13)
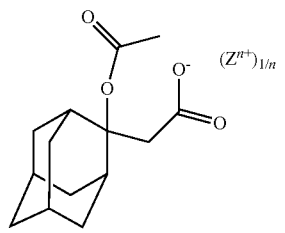
(1-14)
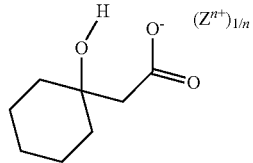
(1-15)

-continued

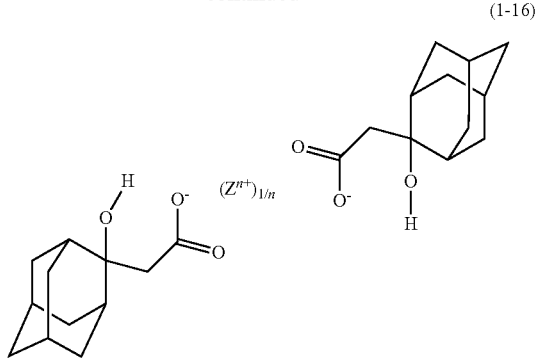

(1-16)

In the above formulae (1-1) to (1-16), $Z^{n+}$ is as defined in the above formula (1).

Synthesis Procedure of Compound (C)

The compound (C) may be synthesized conveniently with a favorable yield according to the following scheme, for example, in a case of a compound represented by the following formula (i-a), wherein $R^1$ represents a hydrogen atom; $R^2$ to $R^5$ each represent a hydrogen atom or a monovalent organic group; and n is 1 in the above formula (1).

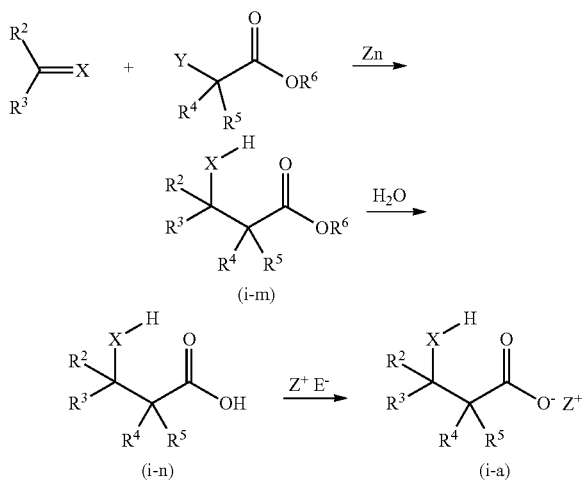

In the above scheme, X represents an oxygen atom or a sulfur atom; $R^2$ to $R^5$ each independently represent a hydrogen atom or a monovalent organic group having 1 to 20 carbon atoms; $R^6$ represents a monovalent organic group having 1 to 20 carbon atoms; Y represents a halogen atom; $Z^+$ represents a monovalent cation; and $E^-$ represents a monovalent anion.

Y represents preferably a chlorine atom or a bromine atom, and more preferably a bromine atom.

By allowing the (thio)carbonyl compound represented by the above formula and the α-halocarboxylic acid ester compound represented by the above formula to react in the presence of zinc and trimethyl silyl chloride in a solvent such as tetrahydrofuran, a β-hydroxy or sulfanyl carboxylic acid ester represented by the above formula (i-m) is obtained. Next, by allowing hydrolysis of the compound (i-m) in the presence of lithium hydroxide in a solvent such as tetrahydrofuran, the carboxylic acid represented by the above formula (i-n) is obtained. Subsequently, the compound (i-n) and a salt represented by $Z^+E^-$ such as a hydrogen carbonate salt are allowed to ion exchange in a solvent such as acetone, whereby the compound (i-a) can be obtained. Furthermore, the hydrogen atom bonding to X in the compound (i-a) may be substituted with an organic group by using an appropriate methylation agent, acetylation agent or the like.

Appropriately purifying the thus obtained product by column chromatography, recrystallization, distillation or the like enables the compound (i-a) to be isolated.

The compound (C) other than the compound (i-a) can be synthesized by a method similar to that described above.

The lower limit of the content of the compound (C) with respect to 100 parts by mass of the polymer (A) is preferably 0.1 parts by mass, more preferably 0.5 parts by mass, still more preferably 0.7 parts by mass, and particularly preferably 1 part by mass. The upper limit of the content is preferably 10 parts by mass, more preferably 5 parts by mass, still more preferably 3 parts by mass, and particularly preferably 2 parts by mass. When the content of the compound (C) falls within the above range, the LWR performance, etc. of the radiation-sensitive resin composition can be further improved.

(D) Solvent

The solvent (D) is not particularly limited as long as it is a solvent capable of dissolving or dispersing at least the polymer (A), the acid generator (B) and the compound (C), and optional component(s), etc., contained as needed.

The solvent (D) is exemplified by an alcohol solvent, an ether solvent, a ketone solvent, an amide solvent, an ester solvent, a hydrocarbon solvent, and the like.

Examples of the alcohol solvent include:

aliphatic monohydric alcohol solvents having 1 to 18 carbon atoms such as 4-methyl-2-pentanol and n-hexanol;

alicyclic monohydric alcohol solvents having 3 to 18 carbon atoms such as cyclohexanol;

polyhydric alcohol solvent having 2 to 18 carbon atoms such as 1,2-propylene glycol;

polyhydric alcohol partially etherated solvents having 3 to 19 carbon atoms such as propylene glycol monomethyl ether; and the like.

Examples of the ether solvent include:

dialkyl ether solvents such as diethyl ether, dipropyl ether, dibutyl ether, dipentyl ether, diisoamyl ether, dihexyl ether and diheptyl ether;

cyclic ether solvents such as tetrahydrofuran and tetrahydropyran;

aromatic ring-containing ether solvents such as diphenyl ether and anisole; and the like.

Examples of the ketone solvent include:

chain ketone solvents such as acetone, methyl ethyl ketone, methyl n-propyl ketone, methyl n-butyl ketone, diethyl ketone, methyl iso-butyl ketone, 2-heptanone, ethyl n-butyl ketone, methyl n-hexyl ketone, di-iso-butyl ketone and trimethylnonanone;

cyclic ketone solvents such as cyclopentanone, cyclohexanone, cycloheptanone, cyclooctanone and methylcyclohexanone;

2,4-pentanedione, acetonylacetone and acetophenone; and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

monocarboxylic acid ester solvents such as n-butyl acetate and ethyl lactate;

polyhydric alcohol carboxylate solvents such as propylene acetate glycol;

polyhydric alcohol partially etherated carboxylate solvents such as propylene glycol monomethyl ether acetate;

polyhydric carboxylic acid diester solvents such as diethyl oxalate;

carbonate solvents such as dimethyl carbonate and diethyl carbonate; and the like.

Examples of the hydrocarbon solvent include:

aliphatic hydrocarbon solvents having 5 to 12 carbon atoms such as n-pentane and n-hexane;

aromatic hydrocarbon solvents having 6 to 16 carbon atoms such as toluene and xylene; and the like.

Of these, the ester solvent or the ketone solvent is preferred, the polyhydric alcohol partially etherated carboxylate solvent or the cyclic ketone solvent is more preferred, and propylene glycol monomethyl ether acetate or cyclohexanone is still more preferred. One, or two or more types of the solvent (D) may be contained.

(E) Polymer

The polymer (E) has a percentage content of fluorine atoms by mass being greater than that of the polymer (A). The polymer having higher hydrophobicity than the polymer (A) as a base resin tends to be localized in the surface layer of a resist film, and the polymer (E) has the percentage content of fluorine atoms by mass being greater than that of the polymer (A). Therefore, due to the characteristics that result from the hydrophobicity, the polymer (E) tends to be localized in the surface layer of the resist film. As a result, the radiation-sensitive resin composition enables elution of the acid generating agent, the acid diffusion control agent and the like into a liquid immersion medium to be inhibited during the liquid immersion lithography. In addition, the radiation-sensitive resin composition enables an advancing contact angle of a liquid immersion medium on the resist film to be adjusted to fall within a desired range owing to the hydrophobicity that results from the characteristics the polymer (E), thereby enabling generation of the bubble defects to be inhibited. Furthermore, the radiation-sensitive resin composition leads to an increase in a receding contact angle of the liquid immersion medium on the resist film, whereby a scanning exposure at a high speed without being accompanied by residual water droplets is enabled. Due to thus containing the polymer (E), the radiation-sensitive resin composition is capable of forming a resist film suited for a liquid immersion lithography process.

The lower limit of the percentage content by mass of fluorine atoms of the polymer (E) is preferably 1% by mass, more preferably 2% by mass, and still more preferably 3% by mass. The upper limit of the percentage content by mass of is preferably 60% by mass, more preferably 50% by mass, and still more preferably 40% by mass. When the percentage content by mass of fluorine atoms falls within the above range, localization of the polymer (E) in the resist film can be more adequately adjusted. It is to be noted that the percentage content by mass of fluorine atoms of the polymer may be calculated based on the structure of the polymer determined by $^{13}$C-NMR spectroscopy.

The mode of the incorporation of the fluorine atom in the polymer (E) is not particularly limited, and the fluorine atom may bond to any of the main chain, a side chain or the end of the polymer (E). The polymer (E) preferably has a structural unit that includes a fluorine atom (hereinafter, may be also referred to as "structural unit (f)"). In light of an improvement of the inhibitory ability of development defects of the radiation-sensitive resin composition, the polymer (E) preferably has, in addition to the structural unit (f), a structural unit that includes an acid-labile group. The structural unit that includes an acid-labile group is exemplified by the structural unit (I) in the polymer (A), and the like.

Moreover, the polymer (E) preferably has an alkali-labile group. When the polymer (E) has the alkali-labile group, the surface of the resist film can be changed effectively from hydrophobic to hydrophilic in a development with an alkali, whereby the inhibitory ability of development defects of the radiation-sensitive resin composition may be more improved. The "alkali-labile group" as referred to herein means a group that substitutes for the hydrogen atom of a carboxy group, a hydroxy group or the like and may be dissociated in an alkaline aqueous solution (for example, a 2.38% by mass aqueous tetramethylammonium hydroxide solution at 23° C.).

The structural unit (f) is preferably a structural unit represented by the following formula (f-1) (hereinafter, may be also referred to as "structural unit (f-1)") or a structural unit represented by the following formula (f-2) (hereinafter, may be also referred to as "structural unit (f-2)"). The structural unit (f) may contain one or two or more types of the structural unit (f-1) or the structural unit (f-2).

Structural Unit (f-1)

The structural unit (f-1) is represented by the following formula (f-1). When the polymer (E) has the structural unit (f-1), the percentage content of fluorine atoms by mass can be adjusted.

(f-1)

In the above formula (f-1), represents a hydrogen atom, a fluorine atom, a methyl group or a trifluoromethyl group; G represents a single bond, an oxygen atom, a sulfur atom, —COO—, —SO$_2$ONH—, —CONH— or —OCONH—; and R$^K$ represents a monovalent fluorinated chain hydrocarbon group having 1 to 6 carbon atoms or a monovalent fluorinated alicyclic hydrocarbon group having 4 to 20 carbon atoms.

In light of the copolymerizability of a monomer that gives the structural unit (f-1), R$^J$ represents preferably a hydrogen atom or a methyl group, and more preferably a methyl group.

G described above represents preferably —COO—, —SO$_2$ONH—, —CONH— or —OCONH—, and more preferably —COO—.

The monovalent fluorinated chain hydrocarbon group having 1 to 6 carbon atoms which may be represented by R$^K$ is exemplified by a linear or branched alkyl group having 1 to 6 carbon atoms, wherein a part or all of hydrogen atoms is/are substituted with a fluorine atom.

The monovalent fluorinated alicyclic hydrocarbon group having 4 to 20 carbon atoms which may be represented by R$^K$ is exemplified by a monocyclic or polycyclic alicyclic hydrocarbon group having 4 to 20 carbon atoms, wherein a part or all of hydrogen atoms is/are substituted with a fluorine atom, and the like.

$R^K$ represents preferably a fluorinated chain hydrocarbon group, more preferably a 2,2,2-trifluoroethyl group or a 1,1,1,3,3,3-hexafluoro-2-propyl group, and still more preferably a 2,2,2-trifluoroethyl group.

In a case in which the polymer (E) has the structural unit (f-1), the lower limit of the proportion of the structural unit (f-1) with respect to the total structural units constituting the polymer (E) is preferably 10 mol %, and more preferably 20 mol %. The upper limit of the aforementioned proportion is preferably 100 mol %, and still more preferably 70 mol %. When the proportion of the structural unit (f-1) falls within the above range, the mass percentage content of fluorine atoms of the polymer (E) can be adjusted further appropriately.

Structural Unit (f-2)

The structural unit (f-2) is represented by the following formula (f-2). When the polymer (E) has the structural unit (f-2), the solubility in an alkaline developer solution is improved, thereby enabling the occurrence of development defects to be inhibited.

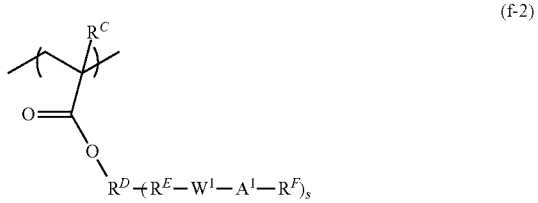

(f-2)

The structural unit (f-2) is generally classified into two forms: (x) a structural unit having an alkali-soluble group; and (y) a structural unit having a group that is to be dissociated by an action of an alkali to increase the solubility in an alkaline developer solution (hereinafter, may be also referred to as "alkali-labile group"). For both the forms (x) and (y), in the above formula (f-2), $R^C$ represents a hydrogen atom, a fluorine atom, a methyl group or a trifluoromethyl group; $R^D$ represents a single bond, a hydrocarbon group having 1 to 20 carbon atoms and having a valency of (s+1), a structure obtained by incorporating an oxygen atom, a sulfur atom, —$NR^{dd}$—, a carbonyl group, —COO— or —CONH— bonded to the end on the $R^E$ side of this hydrocarbon group, or a structure obtained by substituting with an organic group having a hetero atom a part of the hydrogen atoms included in this hydrocarbon group; $R^{dd}$ represents a hydrogen atom or a monovalent hydrocarbon group having 1 to 10 carbon atoms; and s is an integer of 1 to 3, wherein in a case in which s is 1, $R^D$ is other than a single bond.

In a case in which the structural unit (f-2) has the alkali-soluble group (x), $R^F$ represents a hydrogen atom; $A^1$ represents an oxygen atom, —COO—* or —SO$_2$O—*, wherein * denotes a site bonded to $R^F$; $W^1$ represents a single bond, a hydrocarbon group having 1 to 20 carbon atoms or a divalent fluorinated hydrocarbon group, wherein in a case in which $A^1$ represents an oxygen atom, $W^1$ represents a fluorinated hydrocarbon group having a fluorine atom or a fluoroalkyl group at the carbon atom bonded to $A^1$; and $R^E$ represents a single bond or a divalent organic group having 1 to 20 carbon atoms, wherein in a case in which s is 2 or 3, a plurality of $R^E$s are identical or different, a plurality of $W^1$s are identical or different, a plurality of $A^1$s are identical or different and a plurality of $R^F$s are identical or different. When the structural unit (f-2) has the alkali-soluble group (x), affinity to alkaline developer solutions are increased, thereby enabling development defects to be prevented. In the structural unit (f-2) having the alkali-soluble group (x), it is particularly preferred that: $A^1$ represents an oxygen atom; and $W^1$ represents a 1,1,1,3,3,3-hexafluoro-2,2-propanediyl group.

In a case in which the structural unit (f-2) has the alkali-labile group (y), $R^F$ represents a monovalent organic group having 1 to 30 carbon atoms; $A^1$ represents an oxygen atom, —$NR^{aa}$—, —COO—* or —SO$_2$O—*; $R^{aa}$ represents a hydrogen atom or a monovalent hydrocarbon group having 1 to 10 carbon atoms, wherein * denotes a site bonded to $R^F$; $W^1$ represents a single bond or divalent fluorinated hydrocarbon group having 1 to 20 carbon atoms; and $R^E$ represents a single bond or a divalent organic group having 1 to 20 carbon atoms, wherein in a case in which $A^1$ represents —COO—* or —SO$_2$O—*, $W^1$ or $R^F$ has a fluorine atom on the carbon atom bonded to $A^1$ or on the carbon atom adjacent thereto, and in a case in which $A^1$ represents an oxygen atom, $W^1$ and $R^E$ each represent a single bond, $R^D$ represents a structure in which a carbonyl group bonds to the end on the $R^E$ side of the hydrocarbon group having 1 to 20 carbon atoms, $R^F$ represents an organic group having a fluorine atom, and wherein in a case in which s is 2 or 3, a plurality of $R^E$s are identical or different, a plurality of $W^1$s are identical or different, a plurality of $A^1$s are identical or different and a plurality of $R^F$s are identical or different. When the structural unit (f-2) has the alkali-labile group (y), the surface of the resist film can be changed from hydrophobic to hydrophilic in a development step with an alkali. As a result, the affinity to developer solution is greatly increased, whereby more efficient inhibition of development defects is enabled. In the structural unit (f-2) having the alkali-labile group (y) it is particularly preferred that: $A^1$ represents —COO—*; and $R^F$ or $W^1$, or both $R^F$ and $W^1$ has/have a fluorine atom.

In light of the copolymerizability of a monomer that gives the structural unit (f-2), and the like, $R^C$ represents preferably a hydrogen atom or a methyl group, and more preferably a methyl group.

In a case of being a divalent organic group, $R^E$ represents preferably a group having a lactone structure, more preferably a group having a polycyclic lactone structure, and still more preferably a group having a norbornanelactone structure.

In a case in which the polymer (E) has the structural unit (f-2), the lower limit of the proportion of the structural unit (f-2) contained with respect to the total structural units constituting the polymer (E) is preferably 1 mol %, and more preferably 10 mol %. The upper limit of the aforementioned proportion is preferably 70 mol %, and more preferably 50 mol %. When the proportion of the structural unit (f-2) falls within the above range, a more appropriate change of the surface property of a resist film formed from the radiation-sensitive resin composition is enabled from water repellent to hydrophilic through the development with an alkali.

The lower limit of the proportion of the structural unit (f) contained with respect to the total structural units constituting the polymer (E) is preferably 10 mol %, more preferably 20 mol %, and still more preferably 30 mol %. The upper limit of the proportion of the structural unit (f) is preferably 100 mol %, more preferably 90 mol %, and still more preferably 85 mol %.

The lower limit of the structural unit that includes an acid-labile group in the polymer (E) with respect to the total structural units constituting the polymer (E) is preferably 5 mol %, more preferably 10 mol %, and still more preferably 15 mol %. The upper limit of the proportion of the polymer (E) is preferably 90 mol %, more preferably 75 mol %, and still more preferably 50 mol %. When the proportion of the structural unit that includes an acid-labile group falls within the above range, inhibitory ability of development defects of the radiation-sensitive resin composition may be further improved.

In a case in which the radiation-sensitive resin composition contains the polymer (E), the lower limit of the content of the polymer (E) with respect to 100 parts by mass of the polymer (A) is preferably 0.1 parts by mass, more preferably 0.5 parts by mass, still more preferably 1 part by mass, and particularly preferably 2 parts by mass. The upper limit of the aforementioned content is preferably 30 parts by mass, more preferably 20 parts by mass, still more preferably 15 parts by mass, and particularly preferably 10 parts by mass. The radiation-sensitive resin composition may contain one or two or more types of the polymer (E).

The polymer (E) may be synthesized according to a method similar to the aforementioned method for the polymer (A).

The lower limit of the Mw as determined by GPC of the polymer (E) is preferably 1,000, more preferably 3,000, still more preferably 4,000, and particularly preferably 5,000. The upper limit of the Mw is preferably 50,000, more preferably 30,000, still more preferably 20,000, and particularly preferably 10,000. When the Mw of the polymer (E) falls within the above range, the coating characteristics and the inhibitory ability of development defects of the radiation-sensitive resin composition may be improved.

The lower limit of the ratio (Mw/Mn) of the Mw to the Mn as determined by GPC of the polymer (E) is typically 1, and preferably 1.2. The upper limit of the aforementioned ratio is preferably 5, more preferably 3, and still more preferably 2.

Other Optional Component

Other optional component of the radiation-sensitive resin composition is exemplified by other acid diffusion controller, a localization accelerator, a surfactant and the like, other than the compound (C). These other optional components each may be used either alone, or in combination of two or more types thereof.

Other Acid Diffusion Controller

The radiation-sensitive resin composition may contain other acid diffusion controller, as needed. The other acid diffusion controller may be contained in the radiation-sensitive resin composition either in the form of a free compound (hereinafter, may be referred to as "other acid diffusion control agent" as appropriate), in the form incorporated as a part of the polymer, or may be in both of these forms.

The other acid diffusion control agent is exemplified by a compound having one nitrogen atom such as monoalkylamine; a compound having two nitrogen atoms such as ethylene diamine; a compound having three or more nitrogen atoms such as polyethylene imine; an amide group-containing compound such as N,N-dimethylacetamide; a urea compound such as 1,1,3,3-tetramethylurea; a nitrogen-containing heterocyclic compound such as N-(undecylcarbonyloxyethyl)morpholine or N-t-butoxycarbonyl-4-hydroxypiperidine; and the like. Alternatively, as the other acid diffusion control agent, a photolabile base (except for those corresponding to the compound (C)) that generates a weak acid upon an exposure through photosensitization, such as triphenylsulfonium salicylate or triphenylsulfonium 10-camphorsulfonate may be used.

In a case in which the radiation-sensitive resin composition contains the other acid diffusion control agent, the upper limit of the content of the other acid diffusion control agent with respect to 100 parts by mass of the polymer (A) is preferably 5 parts by mass, more preferably 3 parts by mass, and still more preferably 1 part by mass. The radiation-sensitive resin composition may contain one, or two or more types of the other acid diffusion controller.

Localization Accelerator

For example in a case in which the radiation-sensitive resin composition contains the polymer (E), the localization accelerator has an effect of allowing the polymer (E) to be localized more efficiently on the surface of a resist film. When the radiation-sensitive resin composition contains the localization accelerator, the amount of the polymer (E) to be added can be reduced than before. Therefore, elution of the component from the resist film into the liquid immersion liquid can be further inhibited, and liquid immersion lithography by high-speed scanning is enabled at a higher speed is enabled, without being accompanied by deterioration of the LWR performance, etc. As a result, an improvement of hydrophobicity of the surface of the resist film that inhibits defects such as watermark defects that result from the liquid immersion is enabled. As such a localization accelerator, a low-molecular weight compound having a relative permittivity of no less than 30 and no greater than 200 and a boiling point at 1 atm of no less than 100° C. may be used. Specifically, such a compound is exemplified by a lactone compound, a carbonate compound, a nitrile compound, a polyhydric alcohol, and the like.

Examples of the lactone compound include γ-butyrolactone, valerolactone, mevalolactone, norbornanelactone, and the like. Examples of the carbonate compound include propylene carbonate, ethylene carbonate, butylene carbonate, vinylene carbonate, and the like. Examples of the nitrile compound include succinonitrile, and the like. Examples of the polyhydric alcohol include glycerin, and the like.

In a case in which the radiation-sensitive resin composition contains the localization accelerator, the lower limit of the content of the localization accelerator with respect to 100 parts by mass of the total amount of the polymer contained in the radiation-sensitive resin composition is preferably 10 parts by mass, more preferably 15 parts by mass, still more preferably 20 parts by mass, and particularly preferably 25 parts by mass. The upper limit of the aforementioned content is preferably 500 parts by mass, more preferably 300 parts by mass, still more preferably 200 parts by mass, and particularly preferably 100 parts by mass.

Surfactant

The surfactant achieves the effect of improving the coating characteristics, striation, developability, and the like. Examples of the surfactant include nonionic surfactants such as polyoxyethylene lauryl ether, and the like. In a case in which the radiation-sensitive resin composition contains the surfactant, the upper limit of the content of the surfactant with respect to 100 parts by mass of the polymer (A) is preferably 2 parts by mass.

Preparation Procedure of Radiation-Sensitive Composition

The radiation-sensitive composition may be prepared, for example, by mixing at a certain ratio, the polymer (A), the acid generator (B), the compound (C) and the solvent (D), and as needed, the optional component(s) such as the polymer (E) and the like, and preferably filtrating the mixture thus obtained through a filter having a pore size of about 0.2 μm, for example. The lower limit of the solid content concentration of the radiation-sensitive resin composition is preferably 0.1% by mass, more preferably 0.5% by mass, and still more preferably 1% by mass. The upper limit of the solid content concentration is preferably 50% by mass, more preferably 30% by mass, and still more preferably 10% by mass.

Resist Pattern-Forming Method

The resist pattern-forming method according to another embodiment of the present invention includes: the step of applying directly or indirectly on one face of a substrate the radiation-sensitive resin composition of the embodiment of the invention (hereinafter, may be also referred to as "applying step"); the step of exposing the resist film obtained by the applying step (hereinafter, may be also referred to as "exposure step"); and the step of developing the resist film exposed (hereinafter, may be also referred to as "development step").

Since the radiation-sensitive resin composition is used in the resist pattern-forming method, formation of a resist pattern being accompanied by less LWR and higher resolution, and being superior in rectangular configuration of the cross-sectional shape, with inhibited film contraction, is enabled, with a favorable depth of focus attained. Each step will be described below.

Applying Step

In this step, the radiation-sensitive resin composition is applied directly or indirectly on one face of the substrate. Thus, a resist film is formed. The substrate on which the resist film is formed is exemplified by a conventionally well-known substrate such as a silicon wafer, a wafer coated with silicon dioxide or aluminum, and the like. In addition, an organic or inorganic antireflective film disclosed in, for example, Japanese Examined Patent Application, Publication No. H6-12452, Japanese Unexamined Patent Application, Publication No. S59-93448, or the like may be formed on the substrate. An application procedure is exemplified by spin-coating, cast coating, roll-coating, and the like. After the application, prebaking (PB) may be carried out as needed for evaporating the solvent remaining in the coating film. The lower limit of the temperature for PB is preferably 60° C., and more preferably 80° C. The upper limit of the temperature for PB is preferably 140° C., and more preferably 120° C. The lower limit of the time period for PB is preferably 5 sec, and more preferably 10 sec. The upper limit of the time period for PB is preferably 600 sec, and more preferably 300 sec. The lower limit of the average thickness of the resist film formed is preferably 10 nm, and more preferably 20 nm. The upper limit of the average thickness is preferably 1,000 nm, and more preferably 500 nm.

In the case of conducting the liquid immersion lithography, when the radiation-sensitive resin composition does not contain a water repellent polymer additive, for example, a protective film for liquid immersion which is insoluble in the liquid immersion medium may be provided on the formed resist film, for the purpose of preventing a direct contact of the resist film with the liquid immersion medium. As the protective film for liquid immersion, either a solvent-peelable protective film that is peeled by a solvent prior to the development step (see Japanese Unexamined Patent Application, Publication No. 2006-227632), or a developer solution-peelable protective film that is peeled concomitant with the development in the development step (see, PCT International Publication Nos. 2005/069076 and 2006/035790) may be used. However, in light of the throughput, a developer solution-peelable protective film for liquid immersion is preferably used.

Exposure Step

In this step, the resist film obtained by the applying step is exposed. This exposure is carried out by irradiation with an exposure light through a photomask (as the case may be, through a liquid immersion medium such as water). Examples of the exposure light include electromagnetic waves such as visible light rays, ultraviolet rays, far ultraviolet rays, extreme ultraviolet rays (EUV), X-rays and γ-rays; charged particle rays such as electron beams and α-rays, and the like, which may be selected in accordance with a line width of the intended pattern. Of these, far ultraviolet rays, EUV or an electron beam is preferred; an ArF excimer laser beam (wavelength: 193 nm), a KrF excimer laser beam (wavelength: 248 nm), EUV or an electron beam is more preferred; and an ArF excimer laser beam, EUV or an electron beam is still more preferred.

In a case where the exposure is carried out by liquid immersion lithography, examples of the liquid immersion liquid for use in the exposure include water, fluorine-containing inert liquids, and the like. It is preferred that the liquid immersion liquid is transparent to an exposure wavelength, and has a temperature coefficient of the refractive index as small as possible so that distortion of an optical image projected onto the film is minimized. In particular, when an ArF excimer laser beam is used as an exposure light, it is preferred to use water in light of availability and ease of handling thereof in addition to the aforementioned considerations. When water is used, a slight amount of an additive which reduces the surface tension of water and imparts enhanced surfactant power may be added. It is preferred that the additive hardly dissolves a resist film on a wafer and has a negligible influence on an optical coating of an inferior face of a lens. The water for use is preferably distilled water.

It is preferred that post exposure baking (PEB) is carried out after the exposure to promote dissociation of the acid-labile group included in the polymer (A), etc. mediated by the acid generated from the acid generator (B), etc., upon the exposure in exposed regions of the resist film. This PEB enables a difference in solubility of the resist film in a developer solution between the light-exposed regions and light-unexposed regions to be increased. The lower limit of the temperature for PEB is preferably 50° C., and more preferably 80° C. The upper limit of the temperature is preferably 180° C., and more preferably 130° C. The lower limit of the time period for PEB is preferably 5 sec, and more preferably 10 sec. The upper limit of the time period is preferably 600 sec, and more preferably 300 sec.

According to the resist pattern-forming method, since the radiation-sensitive resin composition of the embodiment of the present invention is used, inhibition of contraction of the resist film during PEB is enabled.

Development Step

In this step, the resist film exposed is developed. Accordingly, formation of a predetermined resist pattern is enabled. After the development, washing with a rinse agent such as water or an alcohol, followed by drying is typically carried out. The development procedure in the development step may be carried out by either development with an alkali, or development with an organic solvent. In the case of development with an organic solvent, the radiation-sensitive resin composition is greatly advantageous due to being superior in the inhibitory property of film contraction since the resist pattern is formed in the light-exposed region.

In the case of the development with an alkali, the developer solution for use in the development is exemplified by alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene, 1,5-diazabicyclo-[4.3.0]-5-nonene, etc., and the like. Of these, an aqueous TMAH solution is preferred, and a 2.38% by mass aqueous TMAH solution is more preferred.

In the case of the development with an organic solvent, the developer solution is exemplified by: an organic solvent such as a hydrocarbon solvent, an ether solvent, an ester solvent, a ketone solvent and an alcohol solvent; a solvent containing the organic solvent; and the like. Exemplary organic solvent includes one, or two or more types of the solvents exemplified as the solvent (D) for the radiation-sensitive resin composition, and the like. Of these, the ester solvent or the ketone solvent is preferred. The ester solvent is preferably an acetic acid ester solvent, and more preferably n-butyl acetate. The ketone solvent is preferably a chain ketone, and more preferably 2-heptanone. The lower limit of the content of the organic solvent in the developer solution is preferably 80% by mass, more preferably 90% by mass, still more preferably 95% by mass, and particularly preferably 99% by mass. Components other than the organic solvent in the organic solvent developer solution are exemplified by water, silicone oil, and the like.

Examples of the development procedure include: a dipping procedure in which the substrate is immersed for a given time period in the developer solution charged in a container; a puddle procedure in which the developer solution is placed to form a dome-shaped bead by way of the surface tension on the surface of the substrate for a given time period to conduct a development; a spraying procedure in which the developer solution is sprayed onto the surface of the substrate; a dynamic dispensing procedure in which the developer solution is continuously applied onto the substrate that is rotated at a constant speed while scanning with a developer solution-application nozzle at a constant speed; and the like.

Acid Diffusion Control Agent

The acid diffusion control agent of the embodiment of the present invention is represented by the following formula (1'). Due to having the aforementioned characteristics, the acid diffusion control agent may be suitably used as a component for the acid diffusion control agent in the radiation-sensitive resin composition, thereby enabling the LWR performance, etc. of the radiation-sensitive resin composition to be improved.

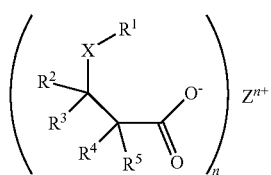

(1')

In the above formula (1'), X represents an oxygen atom or a sulfur atom; $R^1$ represents a hydrogen atom or a monovalent organic group having 1 to 20 carbon atoms; $R^2$ to $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond; $Z^{n+}$ represents a radiation-sensitive cation having a valency of n; and n is an integer of 1 to 3.

Carboxylic Acid Salt

The carboxylic acid salt of the embodiment of the present invention is represented by the following formula (i). The carboxylic acid salt can be suitably used as the acid diffusion control agent described above.

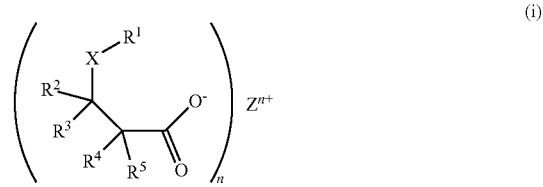

(i)

In the above formula (i), X represents an oxygen atom or a sulfur atom; $R^1$ represents a hydrogen atom or a monovalent organic group having 1 to 20 carbon atoms; $R^2$ to $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond; $Z^{n+}$ represents a radiation-sensitive cation having a valency of n; and n is an integer of 1 to 3.

$R^2$ or $R^3$ in the above formula (i) represents preferably a monovalent organic group having 1 to 20 carbon atoms.

$Z^{n+}$ in the above formula (i) represents preferably an onium cation. The onium cation is preferably a sulfonium cation, an iodonium cation, a tetrahydrothiophenium cation or a combination thereof.

In the above formula (i), n is preferably 2 or 3. Also, in the above formula (i), it is also preferred that n is 1 and $Z^{n+}$ represents an alkali metal cation.

Carboxylic Acid

The carboxylic acid of the embodiment of the present invention is represented by the following formula (i'). The carboxylic acid can be suitably used as a basic ingredient of the carboxylic acid salt of the embodiment of the present invention.

(i')

In the above formula (i'), X represents an oxygen atom or a sulfur atom; $R^1$ represents a hydrogen atom or a monovalent organic group having 1 to 20 carbon atoms; $R^2$ and $R^3$ each independently represent a monovalent organic group having 1 to 20 carbon atoms; $R^4$ and $R^5$ each independently represent a hydrogen atom or a monovalent organic group having 1 to 20 carbon atoms, or two or more of $R^2$ to $R^5$ taken together represent an alicyclic structure having 3 to 20 ring atoms or an aliphatic heterocyclic structure having 3 to 20 ring atoms together with the carbon atom to which the two or more of $R^2$ to $R^5$ bond.

The acid diffusion control agent, the carboxylic acid salt and the carboxylic acid are as described above in the section of Compound (C).

EXAMPLES

Hereinafter, the present invention is explained in detail by way of Examples, but the present invention is not in any way limited to these Examples without departing from the spirit of the invention. Each measurement in Examples and Comparative Examples was undertaken according to the following method.

Weight Average Molecular Weight (Mw) and Number Average Molecular Weight (Mn)

Mw and the Mn of the polymer were determined by gel permeation chromatography (GPC) using GPC columns available from Tosoh Corporation ("G2000 HXL"×2, "G3000 HXL"×1 and "G4000 HXL"×1) under the analytical conditions involving a flow rate: 1.0 mL/min, an elution solvent: tetrahydrofuran, a sample concentration: 1.0% by mass, an amount of injected sample: 100 μL, a column temperature: 40° C., and a detector: differential refractometer, with mono-dispersed polystyrene as a standard. Moreover, the dispersity index (Mw/Mn) was calculated from the results of the determination of the Mw and the Mn.

$^{13}$C-NMR Analysis

An analysis of determining the proportion of each structural unit contained in each polymer (mol %) was performed by using a nuclear magnetic resonance apparatus (JEOL, Ltd., "JNM-ECX400"), with deuterochloroform as a measurement solvent.

Synthesis of Compound (C)

Example 1

Synthesis of Compound (Z-1)

A compound (Z-1) was synthesized according to the following reaction scheme.

Into a reaction vessel, 79.7 mmol of zinc, 2 mmol of trimethyl silyl chloride and 40 g of tetrahydrofuran were charged. After the mixture was stirred at room temperature for 10 min, a solution prepared by dissolving 66.6 mmol of the following compound (ppz-1) and 66.6 mmol of bromomethyl acetate in 10 g of tetrahydrofuran was added dropwise. After the mixture was stirred for 5 hrs, a saturated aqueous ammonium chloride solution was added thereto to terminate the reaction. Ethyl acetate was added to carry out extraction, thereby separating an organic layer. The organic layer thus obtained was washed with a saturated aqueous sodium bicarbonate solution, and then with water. After being dried over anhydrous sodium sulfate, the solvent was distilled off, and purification on column chromatography gave a compound (pz-1) with a favorable yield.

Into a reaction vessel, 22.3 mmol of the compound (pz-1), 40 g of tetrahydrofuran and 4 g of water were charged. Subsequently, 33.5 mmol of lithium hydroxide was added thereto, and the mixture was stirred at room temperature for 6 hrs. Toluene and water were added, and an aqueous layer obtained by liquid separation was neutralized with hydrochloric acid, followed by extraction with ethyl acetate. The organic layer thus obtained was washed with a saturated aqueous sodium chloride solution and dried over anhydrous sodium sulfate. Thereafter the solvent was distilled off to give a compound (z-1) with a favorable yield.

Into a reaction vessel, 6.20 mmol of the compound (z-1) and 5 g of acetone were charged, and the mixture was stirred. Next, 6.30 mmol of a 50% by mass aqueous solution of triphenylsulfonium hydrogencarbonate (TPSHCO$_3$) was added dropwise. After the mixture was stirred for 1 hour, extraction was permitted by adding dichloromethane, and the organic layer was separated. The organic layer thus obtained was dried over anhydrous sodium sulfate and the solvent was distilled off to give a compound (Z-1) with a favorable yield.

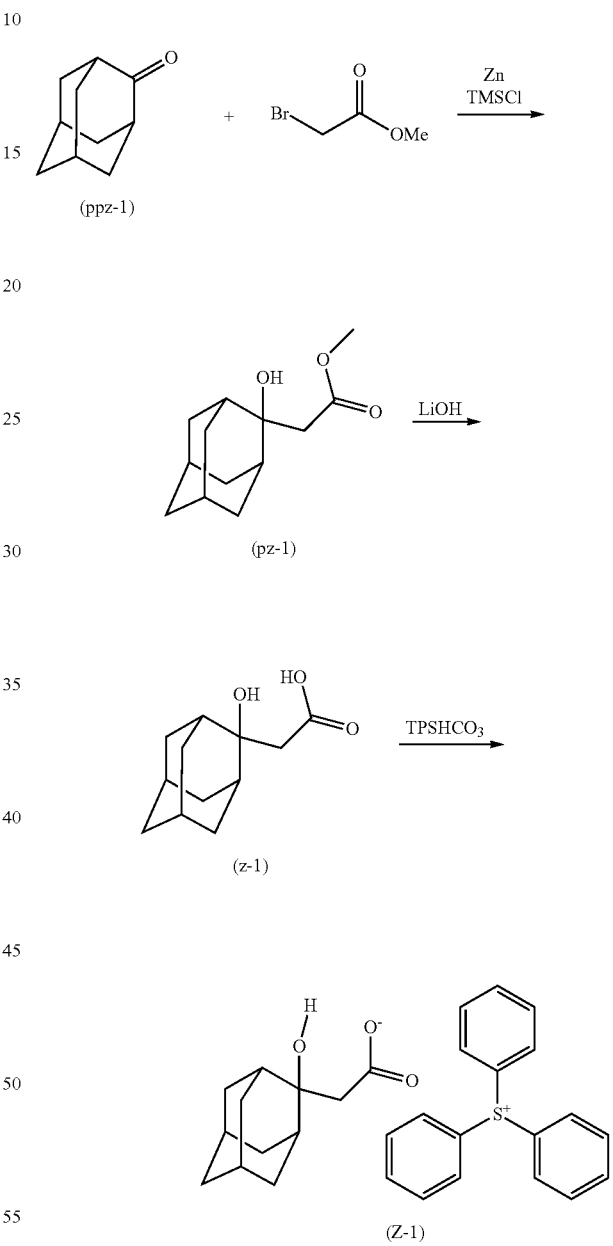

Examples 2 to 16

Syntheses of Compounds (Z-2) to (Z-16)

Compounds (C) represented by the following formulae (Z-2) to (Z-16) were synthesized in a similar manner to Example 1 through appropriately selecting precursors.

(Z-1) 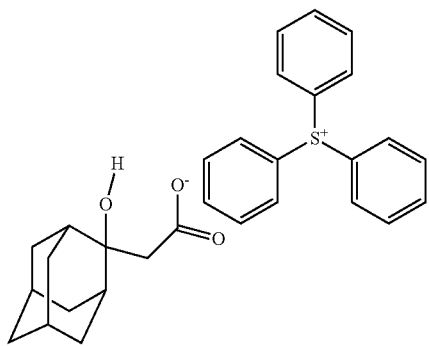
(Z-2) 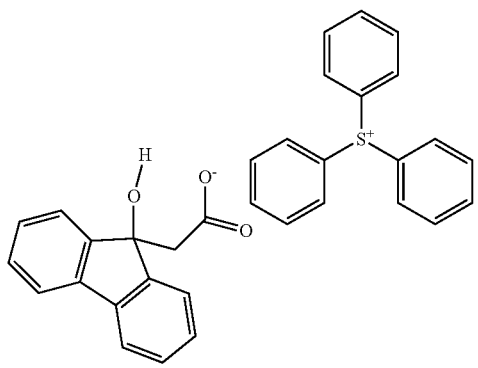
(Z-3) 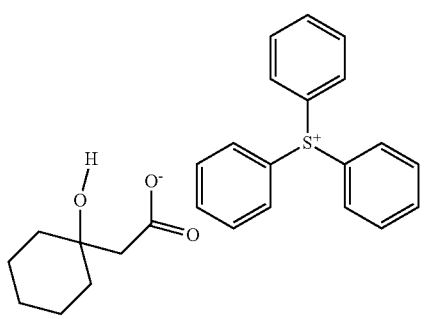
(Z-4) 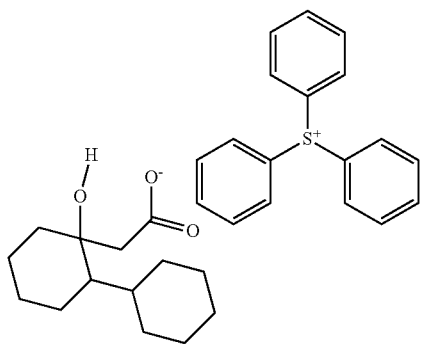
(Z-5) 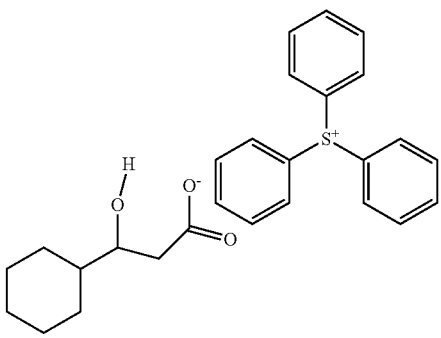
(Z-6) 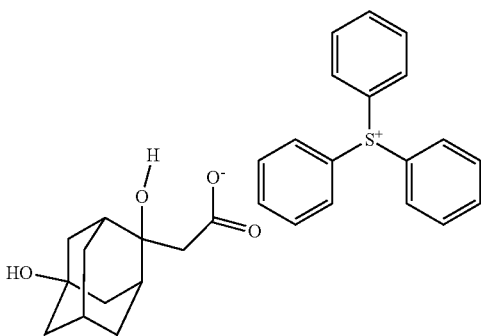
(Z-7) 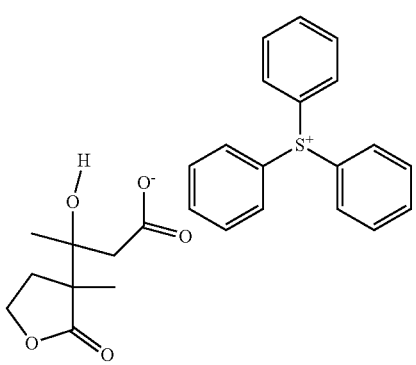
(Z-8) 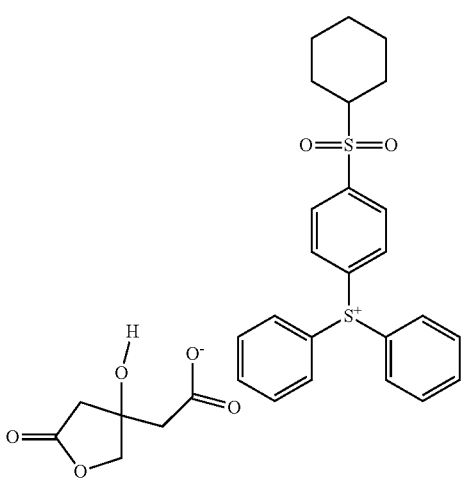

(Z-9)
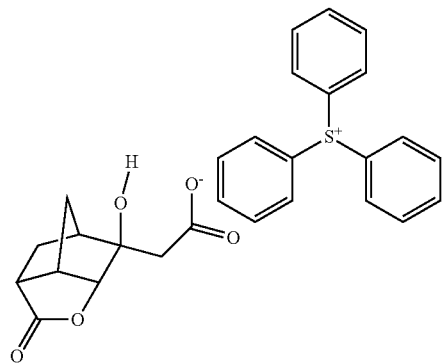
(Z-10)
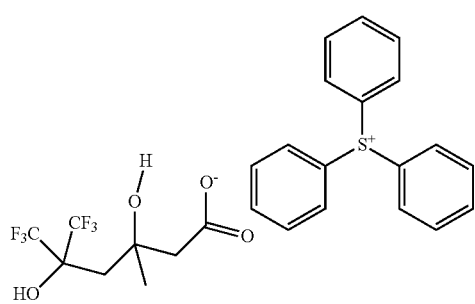
(Z-11)
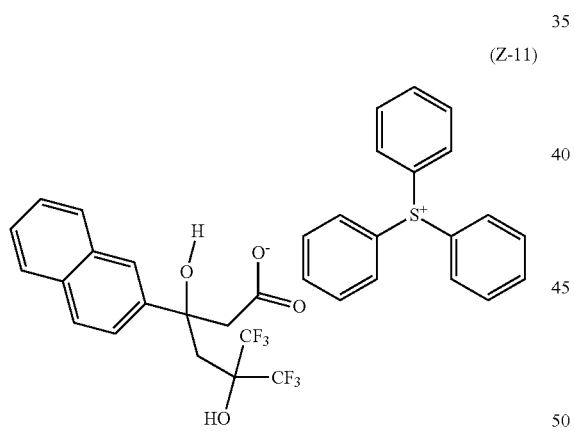
(Z-12)
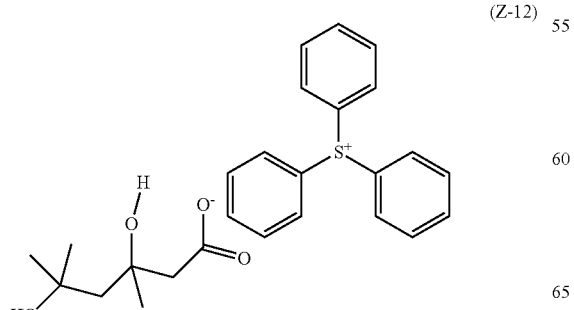
(Z-13)
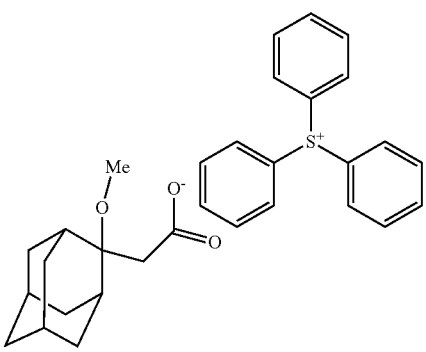
(Z-14)
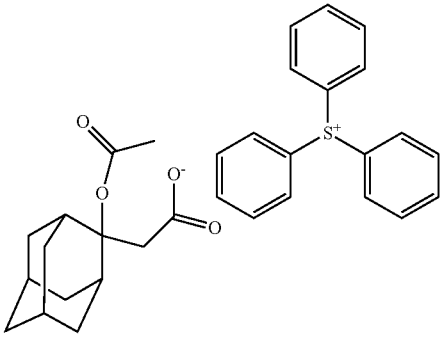
(Z-15)
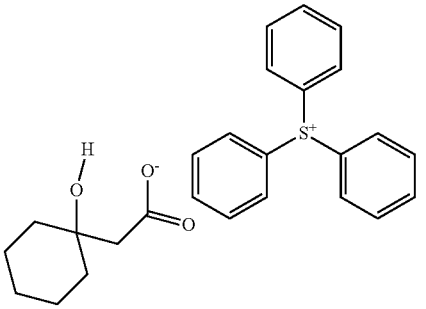
(Z-16)
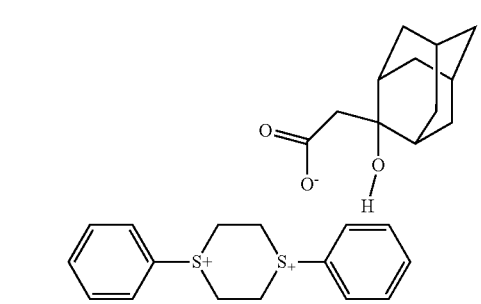
Syntheses of Polymers
Monomers used for the syntheses of the polymer (A) and the polymer (E) are shown below.

Compounds M-3, M-4, M-5 and M-7 that each include a large protecting group having a sterically bulky structure, and compounds M-1, M-2, M-6 and M-16 that each include a small protecting group having a sterically small structure were used as monomers that give the structural unit (I); M-8, M-9, M-11, M-12, M-13 and M-14 were used as monomers that give the structural unit (II); M-10 and M-15 were used as monomers that give the structural unit (III); and M-17 and M-18 were used as monomers that give the other structural unit. In Table 1, "a" appended to M-15 denotes that M-15 becomes a structural unit derived from hydroxystyrene in the polymer (A-8). It is to be noted that in the following Synthesis Examples, unless otherwise specified particularly, the term "parts by mass" means a value, provided that the total mass of the monomers used was 100 parts by mass, and the term "mol %" means a value, provided that the total number of moles of the monomers used accounted for 100 mol %.

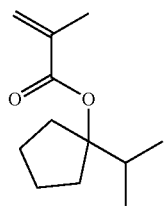

(M-1)

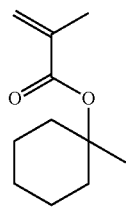

(M-2)

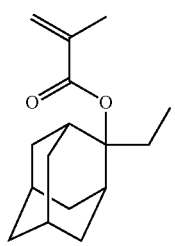

(M-3)

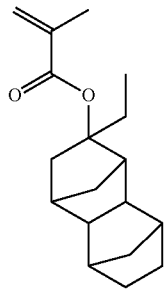

(M-4)

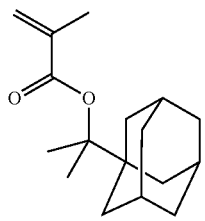

(M-5)

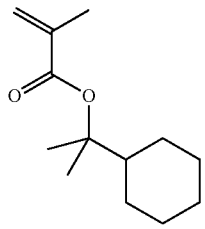

(M-6)

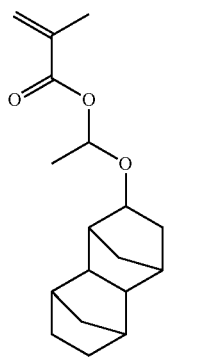

(M-7)

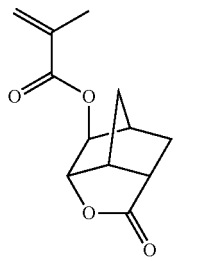

(M-8)

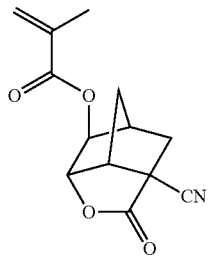

(M-9)

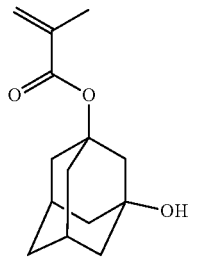

(M-10)

(M-11)
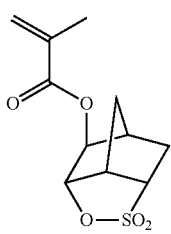

(M-12)
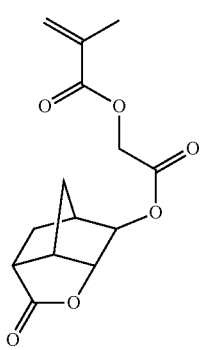

(M-13)
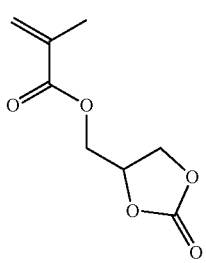

(M-14)
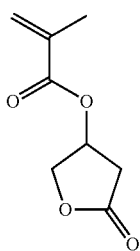

(M-15)
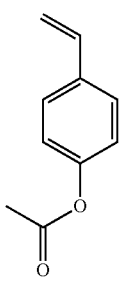

(M-16)
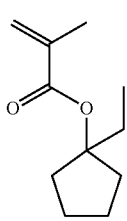

(M-17)
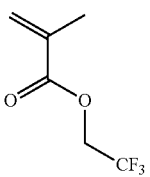

(M-18)
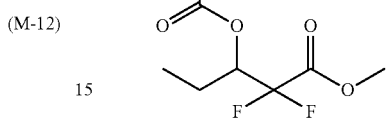

Synthesis of Polymer (A)

Synthesis Example 1

Synthesis of Polymer (A-1)

The compound (M-1) and the compound (M-8) as monomers were dissolved in 2-butanone (200 parts by mass) such that the molar ratio was 50/50. Into the mixture was added azobisisobutyronitrile (AIBN) (5 mol %) as an initiator to prepare a monomer solution. A reaction vessel was charged with 2-butanone (100 parts by mass), and purged with nitrogen for 30 min. The temperature in the reaction vessel was elevated to 80° C., and the monomer solution was added dropwise over 3 hrs with stirring. The time point of the start of the dropwise addition was regarded as the time point of the start of the polymerization reaction, and polymerization reaction was allowed for 6 hrs. After the completion of the polymerization reaction, the polymerization solution was water-cooled to 30° C. or below. The polymerization solution cooled was charged into methanol (2,000 parts by mass), and precipitated white powder was filtered off. The white powder obtained by filtration was washed twice with methanol, followed by filtration and drying at 50° C. for 17 hrs to give white powdery polymer (A-1) (yield: 78.9%). The polymer (A-1) had Mw of 6,100, and Mw/Mn of 1.41. The result of the $^{13}$C-NMR analysis indicated that the proportions of structural units derived from (M-1) and (M-8) were 49.8 mol % and 50.2 mol %, respectively.

Synthesis Examples 2 to 7

Syntheses of Polymers (A-2) to (A-7)

The polymers (A-2) to (A-7) were synthesized by a similar operation to Synthesis Example 1 through appropriately selecting the monomers.

Synthesis Example 8

Synthesis of Polymer (A-8)

The compound (M-1) and the compound (M-15) as monomers were dissolved in propylene glycol monomethyl ether (100 parts by mass) such that the molar ratio was 50/50. Into the mixture were added azobisisobutyronitrile (AIBN) (5 mol %) as an initiator and t-dodecyl mercaptan (38 parts by mass with respect to 100 parts by mass of the initiator) as a chain transfer agent to prepare a monomer solution. The monomer solution was maintained in a nitrogen atmosphere at a reaction temperature of 70° C. to allow for copolymerization for 16 hrs. After the completion of the polymerization reaction, the polymerization solution was added dropwise into n-hexane (1,000 parts by mass) to permit solidification purification of the polymer. Propylene glycol monomethyl ether (150 parts by mass) was again added to the polymer. Thereto were further added methanol (150 parts by mass), triethylamine (1.5 molar equivalent with respect to the amount of the compound (M-10)) and water (1.5 molar equivalent with respect to the amount of the compound (M-10)), and the mixture was subjected to a hydrolysis reaction for 8 hrs while refluxing at a boiling point was allowed. After the completion of the reaction, the solvent and triethylamine were distilled off in vacuo, and the resulting polymer was dissolved in acetone (150 parts by mass), which was then added dropwise to water (2,000 parts by mass) to permit solidification, and the produced white powder was filtered off. Drying at 50° C. for 17 hrs gave a white powdery polymer (A-8) (yield: 72.3%). The polymer (A-8) had Mw of 6,400, and Mw/Mn of 1.72. The result of the $^{13}$C-NMR analysis indicated that that the proportions of structural units derived from (M-1) and (M-15) were 51.2 mol % and 48.8 mol %, respectively.

Synthesis of Polymer (E)

Synthesis Example 9

Synthesis of Polymer (E-1)

The compound (M-16), the compound (M-17) and the compound (M-18) as monomers were dissolved in 2-butanone (67 parts by mass) such that the molar ratio was 20/40/40. Into the mixture was added AIBN (5 mol % with respect to the total of the monomers) as an initiator to prepare a monomer solution. A reaction vessel was charged with 2-butanone (33 parts by mass), and purged with nitrogen for 30 min. The temperature in the reaction vessel was elevated to 80° C., and the monomer solution was added dropwise over 3 hrs with stirring. The time point of the start of the dropwise addition was regarded as the time point of the start of the polymerization reaction, and polymerization reaction was allowed for 6 hrs. After the completion of the polymerization reaction, the polymerization solution was water-cooled to 30° C. or below. To the polymerization reaction liquid, n-hexane (150 parts by mass) was added to dilute homogenously, and thereafter, methanol (600 parts by mass) was charged, followed by blending. Next, distilled water (30 parts by mass) was charged into the mixed liquid, and the mixture was further stirred and left to stand for 30 min. Subsequently, the underlayer was recovered from the mix liquid, and the solvent in the recovered underlayer was replaced with propylene glycol monomethyl ether acetate to give a propylene glycol monomethyl ether acetate solution containing a polymer (E-1) (yield: 72.0%). The polymer (E-1) had Mw of 7,300, and Mw/Mn of 2.00. The result of the $^{13}$C-NMR analysis indicated that the proportions of structural units derived from (M-16), (M-17) and (M-18) in the polymer (E-1) were 20.1 mol %, 38.9 mol % and 41.0 mol %, respectively.

TABLE 1

| | (A) Polymer | (E) Polymer | Monomer that gives structural unit (I) | | | | | | Monomer that gives structural unit other than structural unit (I) | | | Yield (%) | Mw | Mw/Mn |
| | | | small protecting group | | | large protecting group | | | | | | | | |
| | | | type | amount (mol %) | proportion of structural unit (mol %) | type | amount (mol %) | proportion of structural unit (mol %) | type | amount (mol %) | proportion of structural unit (mol %) | | | |
|---|---|---|---|---|---|---|---|---|---|---|---|---|---|---|
| Synthesis Example 1 | A-1 | | M-1 | 50 | 49.8 | — | — | — | M-8 | 50 | 50.2 | 78.9 | 6,100 | 1.41 |
| Synthesis Example 2 | A-2 | | M-2 | 50 | 50.4 | — | — | — | M-9 | 50 | 49.6 | 79.3 | 6,200 | 1.39 |
| Synthesis Example 3 | A-3 | | — | — | — | M-3 | 50 | 48.9 | M-10 | 50 | 51.1 | 82.3 | 6,300 | 1.42 |
| Synthesis Example 4 | A-4 | | — | — | — | M-4 | 50 | 49.5 | M-11 | 50 | 50.5 | 81.2 | 6,200 | 1.43 |
| Synthesis Example 5 | A-5 | | — | — | — | M-5 | 50 | 49.7 | M-12 | 50 | 50.3 | 73.5 | 6,100 | 1.40 |
| Synthesis Example 6 | A-6 | | M-6 | 50 | 50.2 | — | — | — | M-13 | 50 | 49.8 | 70.2 | 6,400 | 1.44 |
| Synthesis Example 7 | A-7 | | — | — | — | M-7 | 50 | 49.2 | M-14 | 50 | 50.8 | 67.4 | 6,200 | 1.45 |
| Synthesis Example 8 | A-8 | | M-1 | 50 | 51.2 | — | — | — | M-15a | 50 | 48.8 | 72.3 | 6,400 | 1.72 |
| Synthesis Example 9 | | E-1 | M-16 | 20 | 20.1 | — | — | — | M-17 | 40 | 38.9 | 72.0 | 7,300 | 2.00 |
| | | | | | | | | | M-18 | 40 | 41.0 | | | |

Preparation of Radiation-Sensitive Resin Composition

The acid generating agent (B), the compound (C), the solvent (D) and the localization accelerator (F) which were used in the preparation of the radiation-sensitive resin composition are shown below.

(B) Acid Generating Agent

Acid generating agents (B-1) to (B-7)

Each structural formula is shown below.

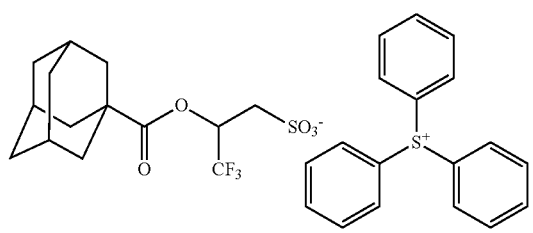

(B-1)

(B-2)
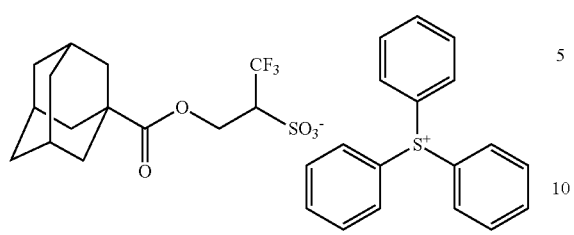
(B-3)
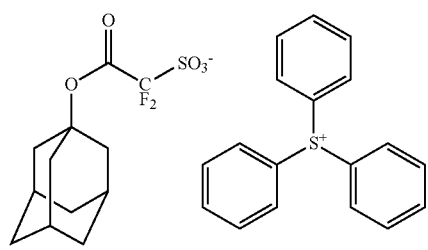
(B-4)
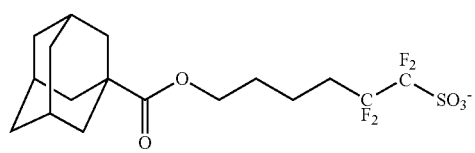
(B-5)
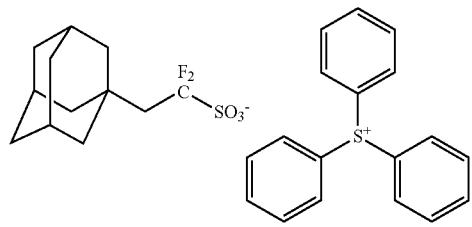
(B-6)
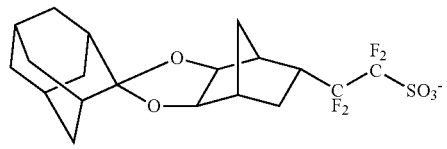
(B-7)
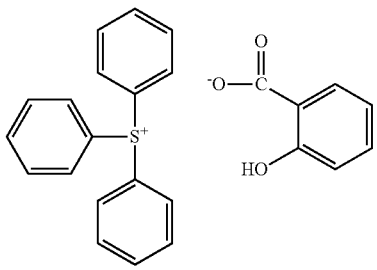
(C) Compound
Compounds used in Examples 17 to 44: the compounds (Z-1) to (Z-16) synthesized in Examples 1 to 16 described above
Compounds used in Comparative Examples 1 to 4: compounds represented by the following formulae (CZ-1) to (CZ-4)
(CZ-1)
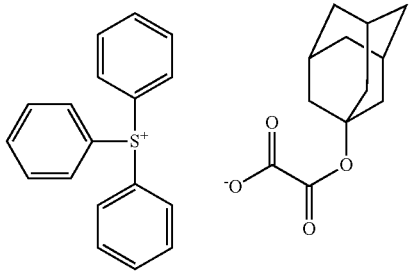
(CZ-2)
(CZ-3)
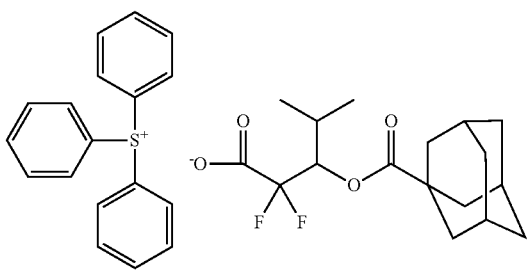
(CZ-4)
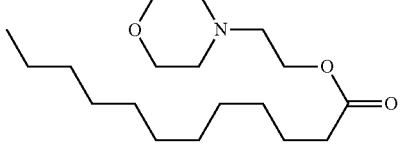

(D) Solvent
D-1: propylene glycol monomethyl ether acetate
D-2: cyclohexanone
(F) Localization Accelerator
F-1: γ-butyrolactone Preparation of Radiation-Sensitive Resin Composition for ArF Exposure Example 17

Preparation of Radiation-Sensitive Resin Composition (J-1)

A radiation-sensitive resin composition (J-1) was prepared by blending 100 parts by mass of (A-1) as the polymer (A), 7.9 parts by mass of (B-1) as the acid generating agent (B), 1.6 parts by mass of (Z-1) as the compound (C), 2,240 parts by mass of (D-1) and 960 parts by mass of (D-2) as the solvent (D), 3 parts by mass of (E-1) as the polymer (E) and 30 parts by mass of (F-1) as the localization accelerator (F), and then filtering the mixture through a membrane filter having a pore size of 0.2 μm.

Examples 18 to 44 and Comparative Examples 1 to 4: Preparation of Radiation-Sensitive Resin Compositions (J-2) to (J-28) and (CJ-1) to (CJ-4)

Each radiation-sensitive resin composition was prepared by a similar operation to that of Example 17 except that the type and the content of each component used were as shown in Tables 2 and 3 below.

TABLE 2

| | Radiation-sensitive resin composition | (A) Polymer type | content (parts by mass) | (B) Acid generating agent type | content (parts by mass) | (C) Compound type | content (parts by mass) | (D) Solvent type | content (parts by mass) | (E) Polymer Type | content (parts by mass) | (F) Localization accelerator Type | content (parts by mass) |
|---|---|---|---|---|---|---|---|---|---|---|---|---|---|
| Example 17 | J-1  | A-1 | 100 | B-1 | 7.9 | Z-1  | 1.6 | D-1/D-2 | 2,240/960 | E-1 | 3 | F-1 | 30 |
| Example 18 | J-2  | A-1 | 100 | B-1 | 7.9 | Z-2  | 1.6 | D-1/D-2 | 2,240/960 | E-1 | 3 | F-1 | 30 |
| Example 19 | J-3  | A-1 | 100 | B-1 | 7.9 | Z-3  | 1.6 | D-1/D-2 | 2,240/960 | E-1 | 3 | F-1 | 30 |
| Example 20 | J-4  | A-1 | 100 | B-1 | 7.9 | Z-4  | 1.6 | D-1/D-2 | 2,240/960 | E-1 | 3 | F-1 | 30 |
| Example 21 | J-5  | A-1 | 100 | B-1 | 7.9 | Z-5  | 1.6 | D-1/D-2 | 2,240/960 | E-1 | 3 | F-1 | 30 |
| Example 22 | J-6  | A-1 | 100 | B-1 | 7.9 | Z-6  | 1.6 | D-1/D-2 | 2,240/960 | E-1 | 3 | F-1 | 30 |
| Example 23 | J-7  | A-1 | 100 | B-1 | 7.9 | Z-7  | 1.6 | D-1/D-2 | 2,240/960 | E-1 | 3 | F-1 | 30 |
| Example 24 | J-8  | A-1 | 100 | B-1 | 7.9 | Z-8  | 1.6 | D-1/D-2 | 2,240/960 | E-1 | 3 | F-1 | 30 |
| Example 25 | J-9  | A-1 | 100 | B-1 | 7.9 | Z-9  | 1.6 | D-1/D-2 | 2,240/960 | E-1 | 3 | F-1 | 30 |
| Example 26 | J-10 | A-1 | 100 | B-1 | 7.9 | Z-10 | 1.6 | D-1/D-2 | 2,240/960 | E-1 | 3 | F-1 | 30 |
| Example 27 | J-11 | A-1 | 100 | B-1 | 7.9 | Z-11 | 1.6 | D-1/D-2 | 2,240/960 | E-1 | 3 | F-1 | 30 |
| Example 28 | J-12 | A-1 | 100 | B-1 | 7.9 | Z-12 | 1.6 | D-1/D-2 | 2,240/960 | E-1 | 3 | F-1 | 30 |
| Example 29 | J-13 | A-1 | 100 | B-1 | 7.9 | Z-13 | 1.6 | D-1/D-2 | 2,240/960 | E-1 | 3 | F-1 | 30 |
| Example 30 | J-14 | A-1 | 100 | B-1 | 7.9 | Z-14 | 1.6 | D-1/D-2 | 2,240/960 | E-1 | 3 | F-1 | 30 |
| Example 31 | J-15 | A-1 | 100 | B-1 | 7.9 | Z-15 | 1.6 | D-1/D-2 | 2,240/960 | E-1 | 3 | F-1 | 30 |
| Example 32 | J-16 | A-1 | 100 | B-1 | 7.9 | Z-16 | 1.6 | D-1/D-2 | 2,240/960 | E-1 | 3 | F-1 | 30 |

TABLE 3

| | Radiation-sensitive resin composition | (A) Polymer type | content (parts by mass) | (B) Acid generating agent type | content (parts by mass) | (C) Compound type | content (parts by mass) | (D) Solvent type | content (parts by mass) | (E) Polymer type | content (parts by mass) | (F) Localization accelerator type | content (parts by mass) |
|---|---|---|---|---|---|---|---|---|---|---|---|---|---|
| Example 33 | J-17 | A-2 | 100 | B-1 | 7.9 | Z-1  | 1.6 | D-1/D-2 | 2,240/960 | E-1 | 3 | F-1 | 30 |
| Example 34 | J-18 | A-3 | 100 | B-1 | 7.9 | Z-1  | 1.6 | D-1/D-2 | 2,240/960 | E-1 | 3 | F-1 | 30 |
| Example 35 | J-19 | A-4 | 100 | B-1 | 7.9 | Z-1  | 1.6 | D-1/D-2 | 2,240/960 | E-1 | 3 | F-1 | 30 |
| Example 36 | J-20 | A-5 | 100 | B-1 | 7.9 | Z-1  | 1.6 | D-1/D-2 | 2,240/960 | E-1 | 3 | F-1 | 30 |
| Example 37 | J-21 | A-6 | 100 | B-1 | 7.9 | Z-1  | 1.6 | D-1/D-2 | 2,240/960 | E-1 | 3 | F-1 | 30 |
| Example 38 | J-22 | A-7 | 100 | B-1 | 7.9 | Z-1  | 1.6 | D-1/D-2 | 2,240/960 | E-1 | 3 | F-1 | 30 |
| Example 39 | J-23 | A-1 | 100 | B-2 | 7.9 | Z-1  | 1.6 | D-1/D-2 | 2,240/960 | E-1 | 3 | F-1 | 30 |
| Example 40 | J-24 | A-1 | 100 | B-3 | 7.9 | Z-1  | 1.6 | D-1/D-2 | 2,240/960 | E-1 | 3 | F-1 | 30 |
| Example 41 | J-25 | A-1 | 100 | B-4 | 7.9 | Z-1  | 1.6 | D-1/D-2 | 2,240/960 | E-1 | 3 | F-1 | 30 |
| Example 42 | J-26 | A-1 | 100 | B-5 | 7.9 | Z-1  | 1.6 | D-1/D-2 | 2,240/960 | E-1 | 3 | F-1 | 30 |
| Example 43 | J-27 | A-1 | 100 | B-6 | 7.9 | Z-1  | 1.6 | D-1/D-2 | 2,240/960 | E-1 | 3 | F-1 | 30 |
| Example 44 | J-28 | A-1 | 100 | B-7 | 7.9 | Z-1  | 1.6 | D-1/D-2 | 2,240/960 | E-1 | 3 | F-1 | 30 |
| Comparative Example 1 | CJ-1 | A-1 | 100 | B-1 | 7.9 | CZ-1 | 1.6 | D-1/D-2 | 2,240/960 | E-1 | 3 | F-1 | 30 |
| Comparative Example 2 | CJ-2 | A-1 | 100 | B-2 | 7.9 | CZ-2 | 1.6 | D-1/D-2 | 2,240/960 | E-1 | 3 | F-1 | 30 |
| Comparative Example 3 | CJ-3 | A-1 | 100 | B-3 | 7.9 | CZ-3 | 1.6 | D-1/D-2 | 2,240/960 | E-1 | 3 | F-1 | 30 |
| Comparative Example 4 | CJ-4 | A-1 | 100 | B-4 | 7.9 | CZ-4 | 1.6 | D-1/D-2 | 2,240/960 | E-1 | 3 | F-1 | 30 |

Resist Pattern Formation

Resist Pattern Formation (1) by ArF Exposure and Development with Alkali

An antireflective film having an average thickness of 105 nm was formed on the surface of a 12-inch silicon wafer by applying a composition for underlayer antireflective film formation ("ARC66" available from Brewer Science) on the surface of the 12-inch silicon wafer using a spin-coater ("CLEAN TRACK ACT12" available from Tokyo Electron Limited), and thereafter baking the composition at 205° C. for 60 sec. Each radiation-sensitive resin composition prepared as described above was applied on the antireflective film using the spin-coater, and subjected to PB at 90° C. for 60 sec. Thereafter, the wafer coated with the radiation-sensitive resin composition was cooled at 23° C. for 30 sec to form a resist film having an average thickness of 90 nm. Next, the resist film was exposed using an ArF excimer laser Immersion Scanner ("NSR-S610C" available from NIKON) through a 40 nm line-and-space (L/S=1/1) mask pattern, under optical conditions involving NA of 1.3 and dipole (Sigma: 0.977/0.782). After the exposure, PEB was carried out on the resist film at 90° C. for 60 sec. Thereafter, the resist film was developed with an alkali by using a 2.38% by mass aqueous TMAH solution as an alkaline developer solution, followed by washing with water and further drying to form a positive resist pattern. In this resist pattern formation, an exposure dose at which a 1:1 line-and-space pattern with a line width of 40 nm was formed through a mask for a 1:1 line-and-space with a target dimension of 40 nm was defined as "optimum exposure dose".

Resist Pattern Formation (2) by ArF Exposure and Development with Organic Solvent A negative-tone resist pattern was formed by a similar operation to that of the Formation of Resist Pattern (1) described above except that: n-butyl acetate was used in place of the aqueous TMAH solution used to execute a development with an organic solvent; and the washing with water was not carried out.

Evaluations

The performance after the ArF exposure of each radiation-sensitive resin composition was evaluated by undertaking the following measurements on the resist pattern formed as described above. It is to be noted that for a line-width measurement of the resist pattern, a scanning electron microscope ("CG-4100" available from Hitachi High-Technologies Corporation) was used.

LWR Performance

The resist pattern was observed from above the pattern by using the scanning electron microscope, and the line width was measured at arbitrary points of 50 in total. A 3σ value was determined from the distribution of the measurements, and the value was defined as "LWR performance (nm)". The smaller value indicates a better LWR performance. The LWR performance may be evaluated to be: "favorable" in a case where the value of the LWR performance was no greater than 4.0 nm; and "unfavorable" in a case where the value of the LWR performance was greater than 4.0 nm.

Resolution

A dimension of the minimum resist pattern was measured which was resolved at the optimum exposure dose, and the measurement was defined as "resolution (nm)". The smaller value indicates a better resolution. The resolution may be evaluated to be: "favorable" in a case where the value of the resolution was no greater than 34 nm; and "unfavorable" in a case where the value of the resolution was greater than 34 nm.

Rectangularity of Cross-Sectional Shape

The cross-sectional shape of the resist pattern which was resolved at the optimum exposure dose was observed, and a line width Lb at the middle portion in an altitude direction of the resist pattern, and a line width La on the top portion of the resist pattern were measured to determine the rectangularity of the cross-sectional shape in terms of the ratio of La to Lb. The rectangularity of cross-sectional shape may be evaluated to be: "A" (favorable) in a case in which $0.9 \leq (La/Lb) \leq 1.1$; and "B" (unfavorable) in a case in which $(La/Lb) < 0.9$ or $1.1 < (La/Lb)$.

Depth of Focus

On the resist pattern which was resolved at the optimum exposure dose, the dimension of a pattern formed when the focus was shifted along the depth direction was observed, a latitude in the depth direction in which the pattern dimension falls within the range of 90% to 110% of the basis without being accompanied by a bridge and/or residue was determined, and the measurement was defined as "depth of focus (nm)". The greater value indicates a more favorable depth of focus. The depth of focus may be evaluated to be: "favorable" in a case in which the measurement was no less than 60 nm; and "unfavorable" in a case in which the measurement was less than 60 nm.

Evaluation of Inhibitory Property of Film Contraction

An antireflective film having an average thickness of 105 nm was formed on the surface of a 12-inch silicon wafer by applying a composition for forming an antireflective film ("ARC66" available from Brewer Science) on the surface of the 12-inch silicon wafer using a spin-coater ("CLEAN TRACK ACT12" available from Tokyo Electron Limited), and thereafter heating the composition at 205° C. for 60 sec. Each radiation-sensitive resin composition prepared as described above was applied on the underlayer antireflective film using the spin-coater, and subjected to PB at 90° C. for 60 sec. Thereafter, the silicon wafer subjected to PB was cooled at 23° C. for 30 sec to form a resist film having an average thickness of 90 nm. Next, the resist film was subjected to overall-exposure at 70 mJ using an ArF excimer laser Immersion Scanner ("NSR-S610C" available from NIKON), and then the film thickness was measured to determine a film thickness A before PEB. Subsequently, PEB was carried out at 90° C. for 60 sec on the resist film after overall-exposure, and thereafter the film thickness was measured again to determine a film thickness B after PEB. From the measurements, $[100 \times (A-B)/A \, (\%)]$ was calculated, which was defined as "inhibitory property of film contraction (%)". The smaller value indicates a better result for a superior inhibitory property of film contraction. The inhibitory property of film contraction may be evaluated to be: "favorable" in a case where the value was no greater than 15%; and "unfavorable" in a case where the value was greater than 15%.

The evaluation results of the performances upon ArF exposure, and the evaluation results of the inhibitory property of film contraction of each radiation-sensitive resin composition are shown in Table 4 below.

TABLE 4

| | Radiation-sensitive resin composition | Development with alkali | | | | Development with organic solvent | | | | Inhibitory property of film contraction (%) |
|---|---|---|---|---|---|---|---|---|---|---|
| | | LWR performance (nm) | resolution (nm) | rectangularity of the cross-sectional shape | depth of focus (nm) | LWR performance (nm) | resolution (nm) | rectangularity of the cross-sectional shape | depth of focus (nm) | |
| Example 17 | J-1 | 3.19 | 31 | 0.99 | 90 | 3.15 | 33 | 0.99 | 90 | 11 |
| Example 18 | J-2 | 3.25 | 32 | 0.97 | 70 | 3.22 | 31 | 1.05 | 90 | 12 |
| Example 19 | J-3 | 3.32 | 33 | 1.01 | 80 | 3.19 | 32 | 0.97 | 90 | 13 |
| Example 20 | J-4 | 3.27 | 32 | 0.99 | 80 | 3.18 | 33 | 1.03 | 80 | 13 |
| Example 21 | J-5 | 3.35 | 33 | 1.00 | 80 | 3.31 | 33 | 1.01 | 80 | 14 |
| Example 22 | J-6 | 3.24 | 31 | 1.00 | 90 | 3.27 | 32 | 1.02 | 80 | 11 |
| Example 23 | J-7 | 3.24 | 31 | 1.01 | 80 | 3.34 | 32 | 1.03 | 90 | 14 |
| Example 24 | J-8 | 3.31 | 32 | 0.97 | 90 | 3.37 | 33 | 1.02 | 80 | 14 |
| Example 25 | J-9 | 3.22 | 31 | 0.99 | 90 | 3.25 | 31 | 0.99 | 90 | 12 |
| Example 26 | J-10 | 3.29 | 32 | 1.01 | 70 | 3.35 | 33 | 0.98 | 70 | 11 |
| Example 27 | J-11 | 3.27 | 33 | 0.97 | 70 | 3.41 | 34 | 1.06 | 80 | 12 |
| Example 28 | J-12 | 3.21 | 34 | 1.02 | 80 | 3.39 | 31 | 1.02 | 90 | 14 |
| Example 29 | J-13 | 3.45 | 34 | 1.03 | 70 | 3.41 | 33 | 0.97 | 70 | 14 |
| Example 30 | J-14 | 3.50 | 33 | 1.03 | 70 | 3.46 | 34 | 0.95 | 70 | 14 |
| Example 31 | J-15 | 3.54 | 34 | 1.02 | 60 | 3.41 | 34 | 0.94 | 60 | 14 |
| Example 32 | J-16 | 3.32 | 32 | 1.01 | 70 | 3.33 | 32 | 1.01 | 80 | 11 |
| Example 33 | J-17 | 3.31 | 31 | 1.01 | 80 | 3.33 | 33 | 1.00 | 80 | 12 |
| Example 34 | J-18 | 3.29 | 33 | 1.03 | 80 | 3.27 | 31 | 1.01 | 80 | 11 |
| Example 35 | J-19 | 3.28 | 32 | 1.01 | 90 | 3.26 | 32 | 0.98 | 90 | 12 |
| Example 36 | J-20 | 3.33 | 32 | 1.02 | 70 | 3.35 | 33 | 0.98 | 80 | 10 |
| Example 37 | J-21 | 3.42 | 33 | 1.01 | 80 | 3.40 | 32 | 0.99 | 70 | 11 |
| Example 38 | J-22 | 3.35 | 31 | 1.00 | 70 | 3.31 | 31 | 1.01 | 80 | 12 |
| Example 39 | J-23 | 3.18 | 31 | 1.02 | 80 | 3.22 | 32 | 1.02 | 70 | 12 |
| Example 40 | J-24 | 3.15 | 32 | 1.01 | 90 | 3.17 | 32 | 1.01 | 80 | 13 |
| Example 41 | J-25 | 3.30 | 33 | 0.98 | 90 | 3.34 | 33 | 1.00 | 80 | 13 |
| Example 42 | J-26 | 3.31 | 32 | 0.98 | 80 | 3.26 | 34 | 0.97 | 80 | 14 |
| Example 43 | J-27 | 3.16 | 32 | 1.02 | 80 | 3.37 | 31 | 0.97 | 70 | 12 |
| Example 44 | J-28 | 3.41 | 32 | 1.01 | 70 | 3.48 | 33 | 0.99 | 80 | 15 |
| Comparative Example 1 | CJ-1 | 4.12 | 36 | 0.89 | 50 | 4.01 | 37 | 1.12 | 40 | 19 |
| Comparative Example 2 | CJ-2 | 4.05 | 35 | 1.12 | 40 | 4.21 | 36 | 0.90 | 50 | 18 |
| Comparative Example 3 | CJ-3 | 4.31 | 37 | 1.11 | 40 | 4.54 | 36 | 1.13 | 40 | 16 |
| Comparative Example 4 | CJ-4 | 4.62 | 38 | 0.85 | 40 | 4.78 | 39 | 1.12 | 30 | 21 |

Preparation of Radiation-Sensitive Resin Composition for Electron Beam Exposure

Example 45

Preparation of Radiation-Sensitive Resin Composition (J-29)

A radiation-sensitive resin composition (J-29) was prepared by blending 100 parts by mass of (A-8) as the polymer (A), 20 parts by mass of (B-1) as the acid generating agent (B), 3.2 parts by mass of (Z-1) as the compound (C), 4,280 parts by mass of (D-1) and 1,830 parts by mass of (D-2) as the solvent (D) and 3 parts by mass of (E-1) as the polymer (E), and then filtering the mixture through a membrane filter having a pore size of 0.2 μm.

Example 46 and Comparative Examples 5 to 8: Preparation of Radiation-Sensitive Resin Compositions (J-30) and (CJ-5) to (CJ-8)

Each radiation-sensitive resin composition was prepared by a similar operation to that of Example 45 except that the type and the content of each component used were as shown in Table 5 below.

TABLE 5

| | Radiation-sensitive resin composition | (A) Polymer | | (B) Acid generating agent | | (C) Compound | | (D) Solvent | | (E) Polymer | |
|---|---|---|---|---|---|---|---|---|---|---|---|
| | | type | content (parts by mass) | type | content (parts by mass) | type | content (parts by mass) | type | content (parts by mass) | type | content (parts by mass) |
| Example 45 | J-29 | A-8 | 100 | B-1 | 20 | Z-1 | 3.2 | D-1/D-2 | 4,280/1,830 | E-1 | 3 |
| Example 46 | J-30 | A-8 | 100 | B-1 | 20 | Z-13 | 3.2 | D-1/D-2 | 4,280/1,830 | E-1 | 3 |
| Comparative Example 5 | CJ-5 | A-8 | 100 | B-1 | 20 | CZ-1 | 3.2 | D-1/D-2 | 4,280/1,830 | E-1 | 3 |
| Comparative Example 6 | CJ-6 | A-8 | 100 | B-1 | 20 | CZ-2 | 3.2 | D-1/D-2 | 4,280/1,830 | E-1 | 3 |
| Comparative Example 7 | CJ-7 | A-8 | 100 | B-1 | 20 | CZ-3 | 3.2 | D-1/D-2 | 4,280/1,830 | E-1 | 3 |

TABLE 5-continued

| Radiation-sensitive resin composition | (A) Polymer type | (A) Polymer content (parts by mass) | (B) Acid generating agent type | (B) Acid generating agent content (parts by mass) | (C) Compound type | (C) Compound content (parts by mass) | (D) Solvent type | (D) Solvent content (parts by mass) | (E) Polymer type | (E) Polymer content (parts by mass) |
|---|---|---|---|---|---|---|---|---|---|---|
| Comparative Example 8 | CJ-8 | A-8 | 100 | B-1 | 20 | CZ-4 | 3.2 | D-1/D-2 | 4,280/1,830 | E-1 | 3 |

Resist Pattern Formation

Resist Pattern Formation (3) by Electron Beam Exposure and Development with Alkali The radiation-sensitive resin composition prepared as described above was applied onto the surface of an 8-inch silicon wafer by using a spin coater (Tokyo Electron Limited, "CLEAN TRACK ACT8"), and then subjected to PB at 90° C. for 60 sec. Thereafter, the silicon wafer was cooled at 23° C. for 30 sec to form a resist film having an average thickness of 50 nm. Next, this resist film was irradiated with an electron beam by using a simplified electron beam writer (Hitachi, Ltd., "HL800D", output: 50 KeV, electric current density: 5.0 A/cm$^2$). After the irradiation, the resist film was subjected to PEB at 130° C. for 60 sec. The resist film was then developed by using a 2.38% by mass aqueous TMAH solution as an alkaline developer solution at 23° C. for 30 sec, followed by washing with water and further drying to form a positive-tone resist pattern.

Evaluations

The performance after the electron beam exposure of each radiation-sensitive resin composition was evaluated by undertaking the following measurements on the resist pattern formed as described above.

Sensitivity

The resist pattern formed as described above was observed from above the pattern by using the scanning electron microscope. An exposure dose at which a line-and-space pattern with a line width of 100 nm was formed was defined as an optimum exposure dose (μC/cm$^2$), and the optimum exposure dose was regarded as sensitivity.

LWR Performance

The resist pattern formed as described above to have a line width of 100 nm (L/S=1/1) was observed from above the pattern by using the scanning electron microscope, and the line width was measured at arbitrary points of 50 in total. A 3σ value was determined from the distribution of the measurements, and the value was defined as "LWR performance (nm)". The smaller value indicates a better LWR performance with less variance of the line width. The LWR performance may be evaluated to be: "favorable" in a case where the value of the LWR performance was no greater than 20 nm; and "unfavorable" in a case where the value of the LWR performance was greater than 20 nm.

TABLE 6

| Radiation-sensitive resin composition | Development with alkali sensitivity (μC/cm$^2$) | Development with alkali LWR performance (nm) |
|---|---|---|
| Example 45 | J-29 | 82 | 16 |
| Example 46 | J-30 | 89 | 15 |
| Comparative Example 5 | CJ-5 | 93 | 23 |
| Comparative Example 6 | CJ-6 | 99 | 22 |
| Comparative Example 7 | CJ-7 | 98 | 21 |
| Comparative Example 8 | CJ-8 | 121 | 38 |

As shown in Table 4 and Table 6, the radiation-sensitive resin compositions of Examples exhibited the LWR performance, the resolution, the rectangularity of the cross-sectional shape, the depth of focus, and the inhibitory property of film contraction all being favorable in the case of carrying out the ArF exposure. Furthermore, the radiation-sensitive resin compositions of Examples exhibited the sensitivity and the LWR performance both being favorable in the case of carrying out the electron beam exposure. Accordingly, the radiation-sensitive resin composition of the embodiment of the present invention is decided to be superior in the LWR performance, the resolution, the rectangularity of the cross-sectional shape, the depth of focus, and the inhibitory property of film contraction. In contrast, at least a part of the aforementioned performances of the radiation-sensitive resin compositions of Comparative Examples was unfavorable. In general, the electron beam exposure has been known to exhibit a similar tendency to an EUV exposure. Therefore, the radiation-sensitive resin compositions of Examples are expected to be superior in the sensitivity and the LWR performance, also in the case of the EUV exposure.

The radiation-sensitive resin composition and the resist pattern-forming method of the embodiments of the present invention enable a resist pattern with less LWR, higher resolution and superior rectangularity of the cross-sectional shape to be formed while attaining a depth of focus and an inhibitory property of film contraction each being superior. The acid diffusion control agent of the embodiment of the present invention can be suitably used as an acid diffusion control agent component of the radiation-sensitive resin composition. The carboxylic acid salt and the carboxylic acid of the embodiments of the present invention can be suitably used as a basic ingredient of the acid diffusion control agent. Therefore, these can be suitably used for working processes of semiconductor devices, and the like, in which microfabrication is expected to be further in progress hereafter.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition, comprising:
a solvent;
a polymer comprising an acid-labile group;
a radiation-sensitive acid generator; and
a compound of formula (1),

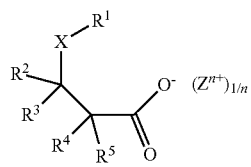

(1)

wherein X is an oxygen atom or a sulfur atom; $R^1$ is a hydrogen atom or a monovalent organic group having 1 to 20 carbon atoms; $R^2$ and $R^3$ are each independently a hydrogen atom, a hydrocarbon group, a hydroxy group-substituted hydrocarbon group, a hydroxy group- and a fluorine atom-substituted hydrocarbon group, or a group comprising an aliphatic heterocyclic structure, or $R^2$ and $R^3$ taken together an alicyclic structure having 3 to 20 ring atoms or an aliphatic heterocyclic structure having 3 to 20 ring atoms together with the carbon atom to which $R^2$ and $R^3$ bond: $R^4$ and $R^5$ are each independently a hydrogen atom or a monovalent organic group having 1 to 20 carbon atoms, and optionally $R^4$ and $R^5$ taken together are an alicyclic structure having 3 to 20 ring atoms or an aliphatic heterocyclic structure having 3 to 20 ring atoms together with the carbon atom to which $R^4$ and $R^5$ bond; $Z^{n+}$ represents a cation having a valency of n; and n is an integer of 1 to 3.

2. The radiation-sensitive resin composition according to claim 1, wherein $R^1$ in the formula (1) is the hydrogen atom.

3. The radiation-sensitive resin composition according to claim 2, wherein $R^2$ and $R^3$ in the formula (1) taken together are an alicyclic structure having 3 to 20 ring atoms or an aliphatic heterocyclic structure having 3 to 20 ring atoms together with the carbon atom to which $R^2$ and $R^3$ bond.

4. The radiation-sensitive resin composition according to claim 2, wherein $R^2$ and $R^3$ in the formula (1) each independently are the group comprising an aliphatic heterocyclic structure, the hydrogen atom, the hydrocarbon group, the hydroxy group-substituted hydrocarbon group, or the hydroxy group- and fluorine atom-substituted hydrocarbon group.

5. The radiation-sensitive resin composition according to claim 2, wherein $R^4$ and $R^5$ in the formula (1) each independently is a hydrogen atom.

6. The radiation-sensitive resin composition according to claim 1, wherein $R^2$ and $R^3$ in the formula (1) taken together are the alicyclic structure having 3 to 20 ring atoms or the aliphatic heterocyclic structure having 3 to 20 ring atoms together with the carbon atom to which $R^2$ and $R^3$ bond.

7. The radiation-sensitive resin composition according to claim 6, wherein $R^4$ and $R^5$ in the formula (1) each independently is a hydrogen atom.

8. The radiation-sensitive resin composition according to claim 1, wherein $R^2$ and $R^3$ in the formula (1) are each independently the group comprising an aliphatic heterocyclic structure, the hydrogen atom, the hydrocarbon group, the hydroxy group-substituted hydrocarbon group, or the hydroxy group- and fluorine atom-substituted hydrocarbon group.

9. The radiation-sensitive resin composition according to claim 8, wherein $R^4$ and $R^5$ in the formula (1) each independently is a hydrogen atom.

10. The radiation-sensitive resin composition according to claim 1, wherein $R^4$ and $R^5$ in the formula (1) is each independently the hydrogen atom.

11. The radiation-sensitive resin composition according to claim 1, wherein the radiation-sensitive acid generator generates sulfonic acid upon irradiation with a radioactive ray.

12. A resist pattern-forming method comprising:
applying the radiation-sensitive resin composition of claim 1 directly or indirectly on one face of a substrate to obtain a resist film;
exposing the resist film; and
developing the resist film exposed.

13. An acid diffusion control agent of formula (1'),

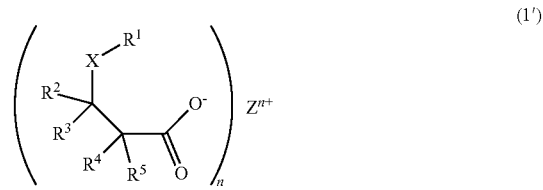

(1')

wherein X is an oxygen atom or a sulfur atom; $R^1$ is a hydrogen atom or a monovalent organic group having 1 to 20 carbon atoms; $R^2$ and $R^3$ are each independently a hydrogen atom, a hydrocarbon group, a hydroxy group-substituted hydrocarbon group, a hydroxy group- and a fluorine atom-substituted hydrocarbon group, or a group comprising an aliphatic heterocyclic structure, or $R^2$ and $R^3$ taken together an alicyclic structure having 3 to 20 ring atoms or an aliphatic heterocyclic structure having 3 to 20 ring atoms together with the carbon atom to which $R^2$ and $R^3$ bond; $R^4$ and $R^5$ are each independently a hydrogen atom or a monovalent organic group having 1 to 20 carbon atoms, and optionally $R^4$ and $R^5$ taken together are an alicyclic structure having 3 to 20 ring atoms or an aliphatic heterocyclic structure having 3 to 20 ring atoms together with the carbon atom to which $R^4$ and $R^5$ bond; $Z^{n+}$ is a radiation-sensitive cation having a valency of n; and n is an integer of 1 to 3.

14. A carboxylic acid salt of formula (i),

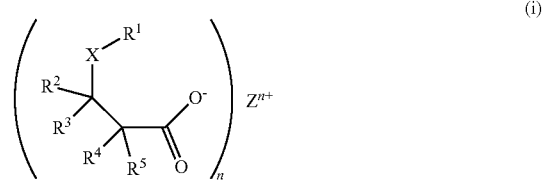

(i)

wherein X is an oxygen atom or a sulfur atom; $R^1$ is a hydrogen atom or a monovalent organic group having 1 to 20 carbon atoms; $R^2$ and $R^3$ are each independently a hydrogen atom, a hydrocarbon group, a hydroxy group-substituted hydrocarbon group, a hydroxy group- and a fluorine atom-substituted hydrocarbon group, or a group comprising an aliphatic heterocyclic structure, or $R^2$ and $R^3$ taken together an alicyclic structure having 3 to 20 ring atoms or an aliphatic heterocyclic structure having 3 to 20 ring atoms together with the carbon atom to which $R^2$ and $R^3$ bond: $R^4$ and $R^5$ are each independently a hydrogen atom or a monovalent organic group having 1 to 20 carbon atoms, and optionally $R^4$ and $R^5$ taken together represent are an alicyclic structure having 3 to 20 ring atoms or an aliphatic heterocyclic structure having 3 to 20 ring atoms together with the carbon atom to which $R^4$ and $R^5$ bond; $Z^{n+}$ is a radiation-sensitive cation having a valency of n; and n is an integer of 1 to 3.

15. The carboxylic acid salt according to claim 14, wherein $R^2$ and $R^3$ in the formula (i) are each independently the group comprising an aliphatic heterocyclic structure, the hydrogen atom, the hydrocarbon group, the hydroxy group-substituted hydrocarbon group, or the hydroxy group- and fluorine atom-substituted hydrocarbon group.

16. The carboxylic acid salt according to claim 14, wherein $Z^{n+}$ in the formula (i) is an onium cation.

17. The carboxylic acid salt according to claim 16, wherein the onium cation is a sulfonium cation, an iodonium cation, a tetrahydrothiophenium cation or a combination thereof.

18. The carboxylic acid salt according to claim 16, wherein n in the formula (i) is 2 or 3.

19. The carboxylic acid salt according to claim 14, wherein
n in the formula (i) is 1, and
$Z^{n+}$ is an alkali metal cation.

20. A carboxylic acid of formula (i'),

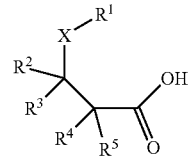

(i')

wherein X is an oxygen atom or a sulfur atom; $R^1$ is a hydrogen atom or a monovalent organic group having 1 to 20 carbon atoms; $R^2$ and $R^3$ are each independently a hydrogen atom, a hydrocarbon group, a hydroxy group-substituted hydrocarbon group, a hydroxy group- and a fluorine atom-substituted hydrocarbon group, or a group comprising an aliphatic heterocyclic structure, or $R^2$ and $R^3$ taken together an alicyclic structure having 3 to 20 ring atoms or an aliphatic heterocyclic structure having 3 to 20 ring atoms together with the carbon atom to which $R^2$ and $R^3$ bond; and $R^4$ and $R^5$ are each independently a hydrogen atom or a monovalent organic group having 1 to 20 carbon atoms, and optionally $R^4$ and $R^5$ taken together are an alicyclic structure having 3 to 20 ring atoms or an aliphatic heterocyclic structure having 3 to 20 ring atoms together with the carbon atom to which $R^4$ and $R^5$ bond.

* * * * *